US 6,946,117 B1

(12) United States Patent
Schutt et al.

(10) Patent No.: US 6,946,117 B1
(45) Date of Patent: *Sep. 20, 2005

(54) STABILIZED PREPARATIONS FOR USE IN NEBULIZERS

(75) Inventors: Ernest G. Schutt, San Diego, CA (US); Thomas E. Tarara, San Diego, CA (US); Luis A. Dellamary, San Marcos, CA (US); Alexey Kabalnov, Corvallis, OR (US); Jeffry G. Weers, San Diego, CA (US)

(73) Assignee: Nektar Therapeutics, San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/218,213

(22) Filed: Dec. 22, 1998

Related U.S. Application Data

(63) Continuation of application No. PCT/US98/20603, filed on Sep. 29, 1998, which is a continuation-in-part of application No. 09/133,848, filed on Aug. 14, 1998, now abandoned, which is a continuation-in-part of application No. 09/106,932, filed on Jun. 29, 1998, now abandoned.

(60) Provisional application No. 60/060,337, filed on Sep. 29, 1997.

(51) Int. Cl.[7] .............................. A61L 9/04; A61F 2/00; A61F 13/00; A61K 9/14; A61K 9/16

(52) U.S. Cl. .......................... 424/45; 424/46; 424/426; 424/434; 424/435; 424/489; 424/490

(58) Field of Search ................................ 424/426, 434, 424/450, 489, 490, 45, 46; 514/937

(56) References Cited

U.S. PATENT DOCUMENTS

| 3,014,844 A | 12/1961 | Thiel et al. .................. 167/82 |
| 4,127,622 A | 11/1978 | Watanabe et al. | |

(Continued)

FOREIGN PATENT DOCUMENTS

| CA | 2036844 | 8/1991 |
| CA | 2136704 | 5/1995 |
| EP | 0 072 046 | 2/1983 |
| EP | 0 274 431 | 7/1988 |
| EP | 0274431 | 7/1988 |
| EP | 0 433 679 | 6/1991 |
| EP | 0372777 | 1/1993 |

(Continued)

OTHER PUBLICATIONS

Lwandiko E. Masinde, et al. *Aerosolized Aqueous Suspensions of Poly(L–Lactic Acid) Microspheres.* 100 International Journal of Pharmaceutics (1993) 123–131.

Donna L. French et al. *The Influence of Formulation on Emission, Deaggregation and Deposition of Dry Powders for Inhalation,* J. Aerosol Sci., vol. 27, No. 5, pp. 769–783 (1996).

(Continued)

*Primary Examiner*—Thurman K. Page
*Assistant Examiner*—S. Tran
(74) *Attorney, Agent, or Firm*—Guy V. Tucker

(57) ABSTRACT

Stabilized dispersions are provided for the delivery of a bioactive agent to the respiratory tract of a patient. The dispersions preferably comprise a stabilized colloidal system which may comprise a fluorochemical component. In particularly preferred embodiments, the stabilized dispersions comprise perforated microstructures dispersed in a fluorochemical suspension medium. As density variations between the suspended particles and suspension medium are minimized and attractive forces between microstructures are attenuated, the disclosed dispersions are particularly resistant to degradation, such as by settling or flocculation. In particularly preferred embodiments, the stabilized dispersions may be administered to the lung of a patient using a nebulizer.

22 Claims, 4 Drawing Sheets

U.S. PATENT DOCUMENTS

| | | | | |
|---|---|---|---|---|
| 4,161,516 | A | 7/1979 | Bell | |
| 4,180,593 | A | 12/1979 | Cohan | |
| 4,590,206 | A | 5/1986 | Forrester et al. | 514/456 |
| 4,818,542 | A | 4/1989 | DeLuca et al. | 424/491 |
| 4,904,479 | A | 2/1990 | Illum | 424/490 |
| 5,011,678 | A | 4/1991 | Wang et al. | 424/45 |
| 5,069,936 | A | 12/1991 | Yen | 427/213.33 |
| 5,118,494 | A | 6/1992 | Schultz et al. | 424/45 |
| 5,126,123 | A | 6/1992 | Johnson | 424/45 |
| 5,145,684 | A * | 9/1992 | Liversidge et al. | 424/489 |
| 5,173,298 | A | 12/1992 | Meadows | 424/427 |
| 5,182,097 | A | 1/1993 | Byron et al. | 424/45 |
| 5,190,029 | A | 3/1993 | Byron et al. | 128/200.14 |
| 5,208,226 | A | 5/1993 | Palmer | 514/171 |
| 5,225,183 | A * | 7/1993 | Purewal et al. | 424/45 |
| 5,230,884 | A | 7/1993 | Evans et al. | 424/45 |
| 5,254,330 | A | 10/1993 | Ganderton et al. | 424/46 |
| 5,260,306 | A | 11/1993 | Boardman et al. | 514/291 |
| 5,284,656 | A | 2/1994 | Platz et al. | 424/435 |
| 5,299,566 | A | 4/1994 | Davis et al. | 128/200.24 |
| 5,308,620 | A | 5/1994 | Yen | 424/484 |
| 5,348,730 | A | 9/1994 | Greenleaf et al. | 424/45 |
| 5,354,934 | A | 10/1994 | Pitt et al. | |
| 5,376,359 | A | 12/1994 | Johnson | 424/46 |
| 5,437,272 | A | 8/1995 | Fuhrman | 128/203.12 |
| 5,470,885 | A | 11/1995 | Fuhrman et al. | 514/743 |
| 5,474,759 | A | 12/1995 | Fassberg et al. | 424/45 |
| 5,490,498 | A | 2/1996 | Faithfull et al. | 128/203.12 |
| 5,492,688 | A | 2/1996 | Byron et al. | 424/45 |
| 5,506,203 | A | 4/1996 | Backstrom et al. | 514/4 |
| 5,518,709 | A | 5/1996 | Sutton et al. | 424/9.52 |
| 5,518,731 | A | 5/1996 | Meadows | 424/427 |
| 5,518,998 | A | 5/1996 | Backstrom et al. | 514/3 |
| 5,547,656 | A | 8/1996 | Unger | 424/9.4 |
| 5,562,608 | A | 10/1996 | Sekins et al. | 604/20 |
| 5,569,450 | A | 10/1996 | Duan et al. | 424/45 |
| 5,580,575 | A | 12/1996 | Unger et al. | 424/450 |
| 5,605,673 | A | 2/1997 | Schutt et al. | 424/9.51 |
| 5,605,674 | A | 2/1997 | Purewal et al. | 424/45 |
| 5,611,344 | A | 3/1997 | Bernstein et al. | |
| 5,612,053 | A | 3/1997 | Baichwal | 424/440 |
| 5,616,311 | A | 4/1997 | Yen | 424/1.33 |
| 5,635,159 | A | 6/1997 | Fu Lu et al. | 424/45 |
| 5,635,161 | A | 6/1997 | Adjei et al. | 424/45 |
| 5,653,961 | A | 8/1997 | McNally et al. | 424/45 |
| 5,653,962 | A | 8/1997 | Akehurst et al. | 424/45 |
| 5,654,007 | A | 8/1997 | Johnson et al. | |
| 5,658,549 | A * | 8/1997 | Akehurst et al. | 424/45 |
| 5,667,809 | A | 9/1997 | Trevino et al. | |
| 5,674,471 | A | 10/1997 | Akehurst et al. | 424/45 |
| 5,674,472 | A | 10/1997 | Akehurst et al. | 424/45 |
| 5,674,473 | A | 10/1997 | Purewal et al. | 424/45 |
| 5,676,929 | A | 10/1997 | Akehurst et al. | 424/45 |
| 5,681,545 | A | 10/1997 | Purewal et al. | 424/45 |
| 5,683,676 | A | 11/1997 | Akehurst et al. | 424/45 |
| 5,683,677 | A | 11/1997 | Purewal et al. | 424/45 |
| 5,688,782 | A | 11/1997 | Neale et al. | 514/180 |
| 5,690,954 | A | 11/1997 | Illum | 424/434 |
| 5,695,743 | A | 12/1997 | Purewal et al. | 424/45 |
| 5,695,744 | A | 12/1997 | Neale et al. | 424/45 |
| 5,707,352 | A | 1/1998 | Sekins et al. | 604/56 |
| 5,718,222 | A | 2/1998 | Lloyd et al. | 128/200.14 |
| 5,718,921 | A | 2/1998 | Mathiowitz et al. | 424/497 |
| 5,720,940 | A | 2/1998 | Purewal et al. | 424/45 |
| 5,724,957 | A | 3/1998 | Rubsamen et al. | 128/200.14 |
| 5,725,841 | A | 3/1998 | Duan et al. | 424/45 |
| 5,725,871 | A | 3/1998 | Illum | 424/434 |
| 5,735,263 | A | 4/1998 | Rubsamen et al. | 128/200.14 |
| 5,736,124 | A | 4/1998 | Akehurst et al. | 424/45 |
| 5,741,478 | A | 4/1998 | Osborne et al. | 424/9.52 |
| 5,741,522 | A | 4/1998 | Violante et al. | 424/489 |
| 5,743,250 | A | 4/1998 | Gonda et al. | 128/200.14 |
| 5,743,252 | A | 4/1998 | Rubsamen et al. | 128/200.14 |
| 5,744,123 | A | 4/1998 | Akehurst et al. | 424/45 |
| 5,744,166 | A | 4/1998 | Illum | 424/501 |
| 5,747,445 | A | 5/1998 | Backstrom et al. | 514/4 |
| 5,755,218 | A | 5/1998 | Johansson et al. | 128/200.14 |
| 5,756,104 | A | 5/1998 | de Haan et al. | 424/206 |
| 5,766,573 | A | 6/1998 | Purewal et al. | 424/45 |
| 5,770,187 | A | 6/1998 | Hasebe et al. | 424/69 |
| 5,770,222 | A | 6/1998 | Unger et al. | 424/450 |
| 5,770,559 | A | 6/1998 | Manning et al. | 514/2 |
| 5,770,585 | A | 6/1998 | Kaufman et al. | |
| 5,804,212 | A | 9/1998 | Illum | 424/434 |
| 5,811,406 | A | 9/1998 | Szoka, Jr. et al. | 514/44 |
| 5,814,607 | A | 9/1998 | Patton | 514/12 |
| 5,817,293 | A | 10/1998 | Akehurst et al. | 424/45 |
| 5,820,883 | A | 10/1998 | Tice et al. | 424/501 |
| 5,830,430 | A | 11/1998 | Unger et al. | 424/1.21 |
| 5,830,853 | A | 11/1998 | Backstrom et al. | 514/4 |
| 5,855,913 | A * | 1/1999 | Hanes et al. | 424/489 |
| 5,856,367 | A | 1/1999 | Barrows et al. | 521/64 |
| 5,858,784 | A | 1/1999 | Debs et al. | 435/375 |
| 5,863,554 | A | 1/1999 | Illum | 424/434 |
| 5,874,063 | A | 2/1999 | Briggner et al. | 424/45 |
| 5,874,064 | A | 2/1999 | Edwards et al. | 424/46 |
| 5,891,844 | A | 4/1999 | Hafner | 514/7 |
| 5,898,028 | A | 4/1999 | Jensen et al. | |
| 5,955,448 | A | 9/1999 | Colaco et al. | |
| 5,985,309 | A | 11/1999 | Edwards et al. | |
| 6,041,777 | A * | 3/2000 | Faithfull et al. | 128/200.24 |
| 6,136,295 | A | 10/2000 | Edwards et al. | |
| RE37,053 | E | 2/2001 | Hanes et al. | |
| 6,290,991 | B1 | 9/2001 | Roser et al. | |
| 6,309,623 | B1 | 10/2001 | Weers et al. | |
| 6,433,040 | B1 * | 8/2002 | Dellamary et al. | 523/218 |
| 6,503,480 | B1 | 1/2003 | Edwards et al. | |
| 6,630,169 | B1 * | 10/2003 | Bot et al. | 424/489 |
| 6,652,837 | B1 | 11/2003 | Edwards et al. | |

FOREIGN PATENT DOCUMENTS

| | | |
|---|---|---|
| EP | 0391896 | 3/1994 |
| EP | 0536204 | 4/1994 |
| EP | 0611567 | 8/1994 |
| EP | 0 611 567 | 8/1994 |
| EP | 0553298 | 11/1994 |
| EP | 0653205 | 5/1995 |
| EP | 0655237 | 5/1995 |
| EP | 0656206 | 6/1995 |
| EP | 0658101 | 6/1995 |
| EP | 0513127 | 7/1995 |
| EP | 0 663 840 | 7/1995 |
| EP | 0493437 | 8/1995 |
| EP | 0556256 | 8/1995 |
| EP | 0616525 | 9/1995 |
| EP | 0499344 | 10/1995 |
| EP | 0 681 843 | 11/1995 |
| EP | 0587790 | 1/1996 |
| EP | 0605578 | 1/1996 |
| EP | 0588897 | 2/1996 |
| EP | 0 743 860 | 11/1996 |
| EP | 0536235 | 1/1997 |
| EP | 0 773 781 | 5/1997 |
| EP | 0539522 | 12/1998 |
| EP | 0 904 056 | 3/1999 |
| GB | 1 265 615 | 3/1972 |
| GB | 2 105 189 | 3/1983 |
| JP | 02084401 | 3/1990 |
| JP | 03264537 | 11/1991 |
| WO | 89/08449 | 9/1989 |
| WO | 90/13285 | 11/1990 |

| | | |
|---|---|---|
| WO | 9104011 | 4/1991 |
| WO | 9111173 | 8/1991 |
| WO | 9112823 | 9/1991 |
| WO | 91/16882 | 11/1991 |
| WO | 9200107 | 1/1992 |
| WO | WO 9211050 A1 * | 7/1992 ........ A61M/15/00 |
| WO | 9211050 | 7/1992 |
| WO | 9214444 | 9/1992 |
| WO | 9218164 | 10/1992 |
| WO | WO 9300951 A1 * | 1/1993 ........ A61M/11/00 |
| WO | 93/00951 | 1/1993 |
| WO | 9311744 | 6/1993 |
| WO | 9311745 | 6/1993 |
| WO | 9314172 | 7/1993 |
| WO | 94/07514 | 4/1994 |
| WO | 9408627 | 4/1994 |
| WO | 9500128 | 1/1995 |
| WO | 95/01324 | 1/1995 |
| WO | 9505194 | 2/1995 |
| WO | 9515118 | 6/1995 |
| WO | 9517195 | 6/1995 |
| WO | 9523613 | 9/1995 |
| WO | 9524892 | 9/1995 |
| WO | 9527476 | 10/1995 |
| WO | 9531182 | 11/1995 |
| WO | 9531964 | 11/1995 |
| WO | 96/03116 | 2/1996 |
| WO | 9609814 | 4/1996 |
| WO | 9615814 | 5/1996 |
| WO | 9618388 | 6/1996 |
| WO | 9619197 | 6/1996 |
| WO | 9619198 | 6/1996 |
| WO | 9619199 | 6/1996 |
| WO | 9619968 | 7/1996 |
| WO | 9626746 | 9/1996 |
| WO | 96/32116 | 10/1996 |
| WO | 9632149 | 10/1996 |
| WO | 96/36314 | 11/1996 |
| WO | 9640068 | 12/1996 |
| WO | 9703649 | 2/1997 |
| WO | 97/13503 | 4/1997 |
| WO | 97/32609 | 9/1997 |
| WO | 9735562 | 10/1997 |
| WO | 9736574 | 10/1997 |
| WO | 9736578 | 10/1997 |
| WO | 9740819 | 11/1997 |
| WO | 9741833 | 11/1997 |
| WO | 9744012 | 11/1997 |
| WO | 9744013 | 11/1997 |
| WO | 9800111 | 1/1998 |
| WO | 9801161 | 1/1998 |
| WO | 9805302 | 2/1998 |
| WO | 9808519 | 3/1998 |
| WO | 9813031 | 4/1998 |
| WO | 9816205 | 4/1998 |
| WO | 9817257 | 4/1998 |
| WO | 98/29096 | 7/1998 |
| WO | 9829097 | 7/1998 |
| WO | 9829098 | 7/1998 |
| WO | 9829099 | 7/1998 |
| WO | 9829140 | 7/1998 |
| WO | 9830207 | 7/1998 |
| WO | 9831346 | 7/1998 |
| WO | 9833480 | 8/1998 |
| WO | 9833487 | 8/1998 |
| WO | WO 9841188 A1 * | 9/1998 |
| WO | 9841188 | 9/1998 |
| WO | 98/51282 | 11/1998 |
| WO | 9906026 | 2/1999 |
| WO | 99/16419 | 4/1999 |
| WO | WO 9916422 A1 * | 4/1999 ........... A61K/9/00 |
| WO | 99/16422 | 4/1999 |

OTHER PUBLICATIONS

Edwards et al., "Large Porous Particles for Pulmonary Drug Delivery," Science, Jun. 20, 1997, 276:1868–1871.

Ph.D. Thesis of Justin Hanes, entitled "Polymer Microspheres for Vaccine Delivery" dated Sep. 1996, archived by the MIT Library Jul. 31, 1997 and catalogued by the MIT Library Dec. 5, 1997.

Hrkach et al., "Synthesis of Poly($_L$–lactic acid–co–$_L$–lysine) Graft Copolymers," Macromolecules 1995, 28(13):4736–4739.

Hrkach et al., "Poly($_L$–lactic acid–co–amino acid) Graft Copolymers: A Class of Functional Biodegradable Biomaterials," Hydrogels and Biodegradable Polymers for Bioapplications (1996), ACS Symposium Seris No. 627, pp. 93–101.

Weers, "Colloidal Particles in Drug Delivery," Current Opinion in Colloid & Interface Science (1998), 3:540–544.

* cited by examiner

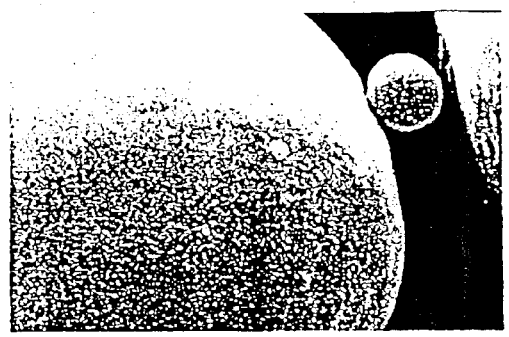 1A1 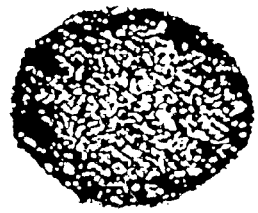 1A2
PFC/PC = 0
 1B1 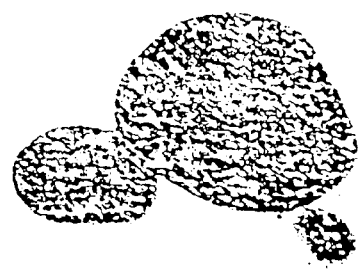 1B2
PFC/PC = 1.1
 1C1 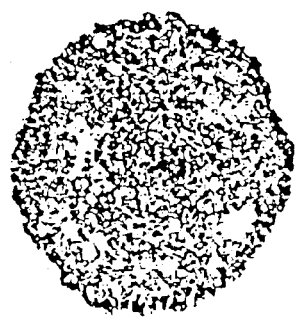 1C2
PFC/PC = 2.2
FIG. 1 (SHEET 1 OF 2)

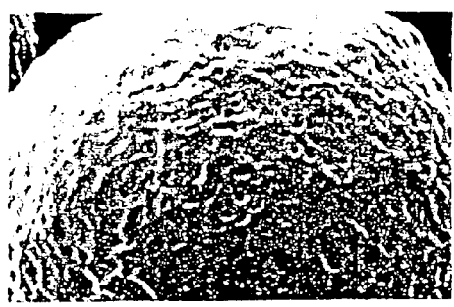
1D1 　　　PFC/PC = 4.8　　　1D2
1E1 　　　PFC/PC = 18.8　　　1E2
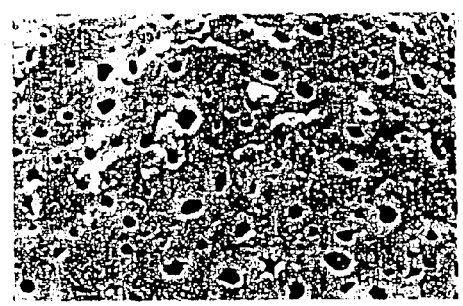
1F1 　　　PFC/PC = 44.7　　　1F2
FIG. 1 (SHEET 2 OF 2)

STABILIZED PREPARATIONS FOR USE IN NEBULIZERS

CROSS REFERENCE TO RELATED APPLICATIONS

The present application, Ser. No. 09/218,213, is a continuation of pending Application No. PCT/US98/20603, filed Sep. 29, 1998, which is a continuation-in-part of application Ser. No. 09/133,848, filed Aug. 14, 1998, now abandoned, which is a continuation-in-part of application Ser. No. 09/106,932, filed Jun. 29, 1998, now abandoned, which claims priority from Provisional Application No. 60/060,337, filed Sep. 29, 1997, now abandoned.

FIELD OF THE INVENTION

The present invention generally relates to formulations and methods for the administration of bioactive agents to a patient via the respiratory tract. More particularly, the present invention relates to methods, systems and compositions comprising relatively stable dispersions that are preferably administered via nebulization both for topical delivery to the lung, and for delivery via the lung to the systemic circulation.

BACKGROUND OF THE INVENTION

Targeted drug delivery means are particularly desirable where toxicity or bioavailability of the pharmaceutical compound is an issue. Specific drug delivery methods and compositions that effectively deposit the compound at the site of action potentially serves to minimize toxic side effects lower dosing requirements and decrease therapeutic costs. In this regard, the development of such systems for pulmonary drug delivery has long been a goal of the pharmaceutical industry.

The three most common systems presently used to deliver drugs locally to the pulmonary air passages are dry powder inhalers (DPIs), metered dose inhalers (MDIs) and nebulizers. MDIs, the most popular method of inhalation administration, may be used to deliver medicaments in a solubilized form or as a dispersion. Typically, MDIs comprise a Freon or other relatively high vapor pressure propellant that forces aerosolized medication into the respiratory tract upon activation of the device. Unlike MDIs, DPIs generally rely on the patient's inspiratory efforts to introduce a medicament in a dry powder form to the lungs. Finally, nebulizers form a medicament aerosol to be inhaled by imparting energy to a liquid solution. More recently, direct pulmonary delivery of drugs during liquid ventilation or pulmonary lavage using a fluorochemical medium has also been explored. While each of these methods and associated systems may prove effective in selected situations, inherent drawbacks, including formulation limitations, can limit their use.

A key development, which has elevated the importance of pulmonary drug delivery systems, has been the emergence of new drugs derived from biotechnology (e.g. peptides, proteins, oligonucleotides and plasmids). The systemic delivery of these biopolymers has proven difficult, owing to their large molecular size, high surface charge, poor chemical and enzymatic stability, and low permeability across various absorption barriers of the body. Because of their low bioavailability by oral and transdermal routes of administration, drugs such as peptides are currently administered primarily by infusions or frequent injections. The development of less invasive methods for delivering peptides and other biopolymers represents a large focus of current drug delivery research, and a number of sites of administration are being explored, including enhanced oral, nasal, and pulmonary delivery.

As indicated above, nebulizers are frequently used for drug delivery to the human lung and are particularly useful for the treatment of hospitalized or nonambulatory patients. There are two main classes of devices: air jet nebulizers and ultrasonic nebulizers. In air jet nebulizers, compressed air is forced through an orifice. A liquid may then be withdrawn from a perpendicular nozzle (the Bernoulli effect) to mix with the air jet to form droplets. A baffle (or series of baffles) within the nebulizer is used to facilitate formation of the aerosol cloud. In contrast, ultrasonic nebulizers rely on the generation of ultrasound waves in an ultrasonic nebulizer chamber by a ceramic piezoelectric crystal that vibrates at a precise frequency when electrically excited. The ultrasonic energy sets up high-energy waves in the nebulizer solution, facilitating generation of an aerosol cloud.

Formulations for nebulization typically comprise aqueous-based solutions. Assuming that the solubility and stability of the active drug are adequate, an aqueous-based formulation administered by nebulization is reasonable when the estimated minimal effective dose exceeds about 200 $\mu$g. Continuous nebulization has long been an option for the delivery of topical lung therapy for the treatment of various lung diseases such as asthma, chronic obstructive pulmonary disease, emphysema, and bronchitis. More recently, proteins such as DNase have been delivered by conventional jet nebulizers for their local effect on the lung. Unfortunately, continuous nebulization is an intrinsically inefficient way to deliver aerosolized medication. This fact is underscored by the observation that doses of bronchodilators delivered using nebulizers are three orders of magnitude greater than a bioequivalent dose delivered by MDI or dry powder generator. In addition to concerns with respect to device efficiency, concerns also exist with regards to changes in the formulation during the nebulization process. For example, drug concentration in the reservoir solution of an air-jet nebulizer often increase over time. Moreover, a change in drug concentration may imply a change in osmolality of the aqueous solution, and hyperosmolar nebulizer solutions have been shown to cause bronchoconstriction.

In terms of pulmonary delivery of bioactive agents to the systemic circulation via nebulization, most of the research has focused on the use of portable hand-held ultrasonic nebulizers, also referred to as metered solution nebulizers. These devices should not be confused with hand-held nebulizers which require several minutes per treatment. These devices, generally known as single-bolus nebulizers, aerosolize a single bolus of medication in an aqueous solution with a particle size efficient for deep lung delivery in one or two breaths. These devices fall into three broad categories. The first category comprises pure piezoelectric single-bolus nebulizers such as those described by Mütterlein, et. al., (J. Aerosol Med. 1988; 1:231). In another category, the desired aerosol cloud may be generated by microchannel extrusion single-bolus nebulizers such as those described in U.S. Pat. No. 3,812,854. Finally, a third category comprises devices exemplified by Robertson, et. al., (WO 92/11050) which describes cyclic pressurization single-bolus nebulizers. Each of the aforementioned references is incorporated herein in their entirety.

While such devices are an improvement over conventional hand-held nebulizers that require treatment times of several minutes, they are somewhat limited by the fact that they employ multidose reservoirs. This is problematic for protein delivery applications where the product must remain sterile throughout the therapy program. At the very least use of these multidose reservoirs would require the use of preservatives, and even this approach is unlikely to be satisfactory under all product usage scenarios. In order to overcome some of these limitations, a unit dose system has recently been described by Schuster, et, al., (Pharm. Res. 1997; 14:354 which is incorporated herein). However, problems remain even with such unit dose systems. For example, a pitfall with devices for the delivery of bioactive agents to the systemic circulation is that the bioactive agent must have long-term stability in an aqueous phase. This is possible only for a select few peptides and proteins.

Accordingly, it is an object of the present invention to provide methods, compositions and systems for the effective pulmonary delivery of bioactive agents using nebulizers.

It is a further object of the present invention to provide methods and compositions for the stabilization of bioactive agents to be delivered using a nebulizer.

It is yet another object of the present invention to provide methods and preparations that advantageously allow for the efficient delivery of bioactive agents to the systemic circulation of a patient in need thereof.

SUMMARY OF THE INVENTION

These and other objects are provided for by the invention disclosed and claimed herein. To that end, the methods and associated compositions of the present invention provide, in a broad aspect, for the improved delivery of bioactive agents using stabilized preparations. Preferably, the bioactive agents are delivered to a patient via the respiratory tract. More particularly, the present invention provides for the formation and use of stabilized dispersions (also referred to as stabilized respiratory dispersions) and inhalation systems, including nebulizers comprising such dispersions, as well as individual components thereof Unlike prior art formulations in a form for use in nebulizers, the present invention preferably employs novel techniques to reduce attractive forces between the dispersed constituents and to reduce density fluctuations in the stabilized dispersion thereby retarding degradation of the disclosed preparations by flocculation, sedimentation or creaming Moreover, the stabilized preparations of the present invention preferably comprise a suspension medium that further serves to reduce the rate of degradation with respect to the incorporated bioactive agent. In particularly preferred embodiments, the suspension medium will comprise a fluorinated compound or fluorocarbon. Those skilled in the art will appreciate that the disclosed stable preparations, and systems comprising those preparations, act to reduce dosing incongruities, thereby facilitating uniform drug delivery, allowing for more concentrated dispersions and retarding the degradation of any labile biopolymers incorporated therein.

In a broad sense, the stabilized dispersions of the present invention incorporate colloidal preparations comprising a nonaqueous continuous phase wherein the stabilized dispersions are capable of being nebulized or aerosolized to provide effective dosing to a patient in need thereof. For example, the stabilized dispersions may comprise any reverse emulsion or particulate dispersion that allows for the effective delivery of a bioactive agent to the pulmonary air passages of a mammal. Those skilled in the art will appreciate that, the disperse phase of such preparations may comprise liquid particulates in the case of reverse emulsions or non-liquid particulates in the case of stabilized suspensions. Accordingly, for the purposes of the present application the term "stabilized dispersion" shall be held to comprise colloidal systems comprising reverse emulsions and particulate suspensions unless otherwise dictated by contextual constraints. With respect to each of these cases, the stabilized dispersion may be used with a nebulizer to provide the desired aerosolized medicament for pulmonary administration.

With regard to particularly preferred embodiments, the stabilized preparations of the present invention provide these and other advantages through the use of particulate suspensions comprising hollow and/or porous perforated microstructures that substantially reduce attractive molecular forces, such as van der Waals forces, which dominate prior art dispersion preparations. More particularly, the use of perforated (or porous) microstructures or microparticulates that are permeated or filled by the surrounding fluid medium, or suspension medium, significantly reduces disruptive attractive forces between the particles. Additionally, the components of the dispersions may be selected to minimize differences in polarizabilities (i.e. reduced Hamaker constant differentials) and further stabilize the preparation. The relatively homogeneous nature of these particulate dispersions or suspensions, inhibits deterioration thereby allowing for pharmaceutical preparations having enhanced stability.

In addition to the heretofore unappreciated advantages associated with the formation of stabilized particulate dispersions, the perforated configuration and corresponding large surface area enables the microstructures to be more easily carried by the flow of gases during inhalation than non-perforated particles of comparable size. This, in turn, enables the perforated microstructures or microparticles of the present invention to be carried more efficiently into the lungs of a patient than non-perforated structures such as micronized particles or relatively nonporous microspheres. In view of these advantages, dispersions comprising perforated microstructures are particularly compatible with inhalation therapies comprising administration of the bioactive preparation to at least a portion of the pulmonary air passages. For the purposes of the present application, these stabilized dispersions intended for pulmonary drug delivery may be termed respiratory dispersions. In particularly preferred embodiments, such respiratory dispersions are used in conjunction with nebulizers to effectively deliver a bioactive agent to the pulmonary air passages or nasal passages of a patient.

For those embodiments comprising perforated microstructures, those skilled in the art will appreciate that they may be formed of any biocompatible material providing the desired physical characteristics or morphology that allows for the preparation of stabilized dispersions. In this respect, the perforated microstructures comprise pores, voids, defects or other interstitial spaces that allow the fluid suspension medium to freely permeate, or perfuse, the particulate boundary, thus reducing or minimizing density differences between the dispersion components. Yet, given these constraints, it will be appreciated that any material or configuration may be used to form the microstructure matrix. With regard to the selected materials, it is desirable that the microstructure incorporates at least one surfactant. Preferably, this surfactant will comprise a phospholipid or other surfactant approved for pulmonary use. As to the configuration, particularly preferred embodiments of the invention incorporate spray dried, hollow microspheres having a relatively thin porous wall defining a large internal void, although, other void containing or perforated structures are contemplated as well.

Accordingly, select embodiments of the invention provide for stable respiratory dispersions for use in a nebulizer comprising a suspension medium having dispersed therein a plurality of perforated microstructures comprising at least one bioactive agent wherein said suspension medium substantially permeates said perforated microstructures.

While preferred embodiments of the invention comprise perforated microstructures, relatively nonporous or solid particulates may also be used to prepare dispersions that are compatible with the teachings herein. That is, respiratory dispersions comprising suspensions of relatively nonporous or solid particulates in a nonaqeous suspension medium are also contemplated as being within the scope of the present invention. In this respect, such relatively nonporous particulate may comprise micronized particles or nanocrystals. Accordingly, as used herein the term "particulate" shall be interpreted broadly to mean any non-liquid particle comprising the discontinuous phase of a dispersion or suspension. More specifically, it will be appreciated that the term "particulate" shall be held to comprise particles of any porosity, including both perforated microstructures and relatively nonporous particles.

It should further be appreciated that the nonaqueous continuous phase or suspension medium, may be any liquid or compound that is in liquid form, under appropriate thermodynamic conditions, for formation of a compatible particulate dispersion or reverse emulsion. Unless otherwise dictated by contextual restraints, the terms "suspension medium," "suspension media" and "nonaqueous continuous phase" are held to be equivalent for the purposes of the instant application and may be used interchangeably. For embodiments wherein the stabilized dispersion is to be used in conjunction with a nebulizer, the suspension medium preferably comprises hydrocarbons or fluorocarbons having a vapor pressure less than about one atmosphere. That is, it will preferably be a liquid under standard conditions of one atmosphere and 25° C.

In accordance with the teachings herein, particularly preferred suspension mediums or nonaqueous continuous phases comprise fluorochemicals (e.g. perfluorocarbons or fluorocarbons) that are liquid at room temperature. It is well established that many fluorochemicals have a proven history of safety and biocompatibility in the lung. Further, in contrast to aqueous solutions, fluorochemicals do not negatively impact gas exchange. Moreover, because of their unique wettability characteristics, fluorochemicals may be able to carry an aerosolized stream of particles deeper into the lung, thereby improving systemic delivery. Finally, many fluorochemicals are also bacteriostatic thereby decreasing the potential for microbial growth in compatible nebulizer devices.

As such, the present invention provides for the use of a liquid fluorochemical in the manufacture of a medicament for the pulmonary delivery of a bioactive agent whereby the medicament comprises a stabilized dispersion having a fluorochemical continuous phase which is nebulized using a nebulizer to form an aerosolized medicament comprising said bioactive agent wherein said aerosolized medicament is administered to at least a portion of the pulmonary air passages of a patient in need thereof.

It will further be appreciated that, in selected embodiments, the present invention comprises methods for forming dispersions which comprise combining a plurality of particulates comprising at least one bioactive agent with a predetermined volume of suspension medium, to provide a respiratory blend. The respiratory blend may then be mixed or otherwise agitated to provide a substantially homogeneous dispersion. Again, in preferred embodiments, the particulates will comprise perforated microstructures which allow for the perfusion or permeation of the selected suspension medium. Of course, in other embodiments the dispersion may comprise a reverse emulsion.

As such, preferred embodiments of the invention provide for the formation of stabilized respiratory dispersions comprising the steps of:

combining a plurality of perforated microstructures comprising at least one bioactive agent with a predetermined volume of a nonaqueous suspension medium to provide a respiratory blend wherein said suspension medium permeates said perforated microstructures; and mixing said respiratory blend to provide a substantially homogeneous respiratory dispersion.

Along with the aforementioned advantages, the stability of the formed particulate dispersions may be further increased by reducing, or minimizing, the Hamaker constant differential between incorporated particulates, or perforated microstructures, and the suspension medium. Those skilled in the art will appreciate that Hamaker constants tend to scale with refractive indices. In this regard, the present invention further provides methods for stabilizing a respiratory dispersion by reducing attractive van der Waals forces comprising the steps of:

providing a plurality of perforated microstructures;

combining the perforated microstructures with a suspension medium comprising at least one fluorochemical wherein the suspension medium and the perforated microstructures are selected to provide a refractive index differential value of less than about 0.5. In accordance with the teachings herein, the particulates preferably comprise perforated microstructures and, in particularly preferred embodiments, the particulates Will comprise hollow, porous microspheres.

With regard to delivery of the stabilized preparations, another aspect of the present invention is directed to liquid inhalation systems for the administration of one or more bioactive agents to a patient. As such, the present invention provides for inhalation systems for the pulmonary administration of a bioactive agent to a patient comprising:

a fluid reservoir;

a stable respiratory dispersion in said fluid reservoir wherein said stabilized dispersion comprises a fluorochemical continuous phase and at least one bioactive agent; and a nebulizer operably associated with said fluid reservoir wherein the nebulizer is capable of aerosolizing and discharging the stable respiratory dispersion.

The respiratory dispersion may comprise a reverse emulsion, microemulsion or particulate suspension. Preferably, the dispersion comprises a suspension medium having dispersed therein a plurality of perforated microstructures, which comprise at least one bioactive agent and are substantially permeated by the suspension medium. Those skilled in the art will appreciate that the nebulizer may comprise an ultrasonic nebulizer, an air jet nebulizer and, most preferably, a single-bolus nebulizer. In any event, the disclosed systems of the present invention allow for the reproducible administration of bioactive agents having aerosolized particle size small enough to travel deep within the lung. More specifically, the aerosolized medicament will preferably exhibit a fine particle fraction of greater than approximately 20% w/w.

Yet another associated advantage of the present invention is the effective pulmonary delivery of bioactive agents. As used herein, the terms "bioactive agent" refers to a substance which is used in connection with an application that is therapeutic or diagnostic in nature, such as methods for diagnosing the presence or absence of a disease in a patient and/or methods for treating disease in a patient. As to compatible bioactive agents, those skilled in the art will appreciate that any therapeutic or diagnostic agent may be incorporated in the stabilized dispersions of the present invention. For example, the bioactive agent may be selected from the group consisting of antiallergics, bronchodilators, bronchoconstrictors, pulmonary lung surfactants, analgesics, antibiotics, leukotriene inhibitors or antagonists, anticholinergics, mast cell inhibitors, antihistamines, antiinflammatories, antineoplastics, anesthetics, antituberculars, imaging agents, cardiovascular agents, enzymes, steroids, genetic material, viral vectors, antisense agents, proteins, peptides and combinations thereof. Particularly preferred bioactive agents comprise compounds which are to be administered systemically (i.e. to the systemic circulation of a patient) such as peptides, proteins or polynucleotides. As will be disclosed in more detail below, the bioactive agent may be incorporated, blended in, coated on or otherwise associated with the perforated microstructure. In other embodiments, the bioactive agent may be associated with the disperse phase (e.g., aqueous phase) of a reverse emulsion.

Whatever form of stabilized dispersion is employed, the present invention provides methods for the pulmonary delivery of one or more bioactive agents comprising the steps of:

providing a stabilized respiratory dispersion comprising one or more bioactive agents wherein the respiratory dispersion comprises a fluorochemical continuous phase;

nebulizing said respiratory dispersion with a nebulizer to provide an aerosolized medicament; and administering a therapeutically effective amount of said aerosolized medicament to at least a portion of the pulmonary passages of a patient in need thereof.

When the stabilized dispersion comprises a reverse emulsion, the bioactive agent preferably will be substantially associated with the dispersed droplets. With respect to particulate dispersions, the selected bioactive agent, or agents, may be used as the sole structural component of the particulates or perforated microstructures. Conversely, the particulates, or perforated microstructures, may comprise one or more components (i.e. structural materials, surfactants, excipients, etc.) in addition to the incorporated bioactive agents. In particularly preferred embodiments, the suspended particulates or perforated microstructures will comprise relatively high concentrations of surfactant (greater than about 10% w/w) along with the incorporated bioactive agent(s). Finally, it should be appreciated that the particulate or perforated microstructure may be coated, linked or otherwise associated with the bioactive agent in a non-integral manner. Whatever configuration is selected, it will be appreciated that the associated bioactive agent may be used in its natural form, or as one or more salts known in the art.

In addition to reverse emulsions and suspensions of perforated microstructures, it must be emphasized that the present invention provides for the nebulization and pulmonary delivery of relatively stable particulate dispersions. Those skilled in the art will appreciate that, due to other physiochemical characteristics, the morphology of incorporated particulates may vary without destabilizing the dispersion. As such, stabilized dispersions may be formed with compatible particulates even if they exhibit relatively low porosity, or are substantially solid. That is, while particularly preferred embodiments of the present invention will comprise perforated microstructures or microspheres, acceptable dispersions may be formed using relatively low porosity articulates such as nanocrystals, or micronized drugs. In this respect, such embodiments are specifically contemplated as being within the scope of the present invention.

The stabilized dispersions of the invention may optionally comprise one or mote additives to further enhance stability or increase biocompatibility. For example, various surfactants, co-solvents, osmotic agents, stabilizers, chelators, buffers, viscosity modulators, solubility modifiers and salts can be associated with the perforated microstructure, suspension medium, or both. The use of such additives will be understood to those of ordinary skill in the art and, the specific quantities, ratios, and types of agents can be determined empirically without undue experimentation.

Other objects, features and advantages of the present invention will be apparent to those skilled in the art from a consideration of the following detailed description of preferred exemplary embodiments thereof.

BRIEF DESCRIPTION OF THE DRAWINGS

FIGS. 1A1 to 1F2 illustrate changes in particle morphology as a function of variation in the ratio of fluorocarbon blowing agent to phospholipid (PFC/PC) present in the spray dry feed. The micrographs, produced using scanning electron microscopy and transmission electron microscopy techniques, show that in the absence of FCs, or at low PFC/JPC ratios, the resulting spray dried microstructures comprising gentamicin sulfate are neither particularly hollow nor porous. Conversely, at high PFC/PC ratios, the particles contain numerous pores and are substantially hollow with thin walls.

FIG. 2 is a scanning electron microscopy image of perforated microstructures comprising cromolyn sodium illustrating a preferred hollow/porous morphology.

DETAILED DESCRIPTION PREFERRED EMBODIMENTS

Figure 2:
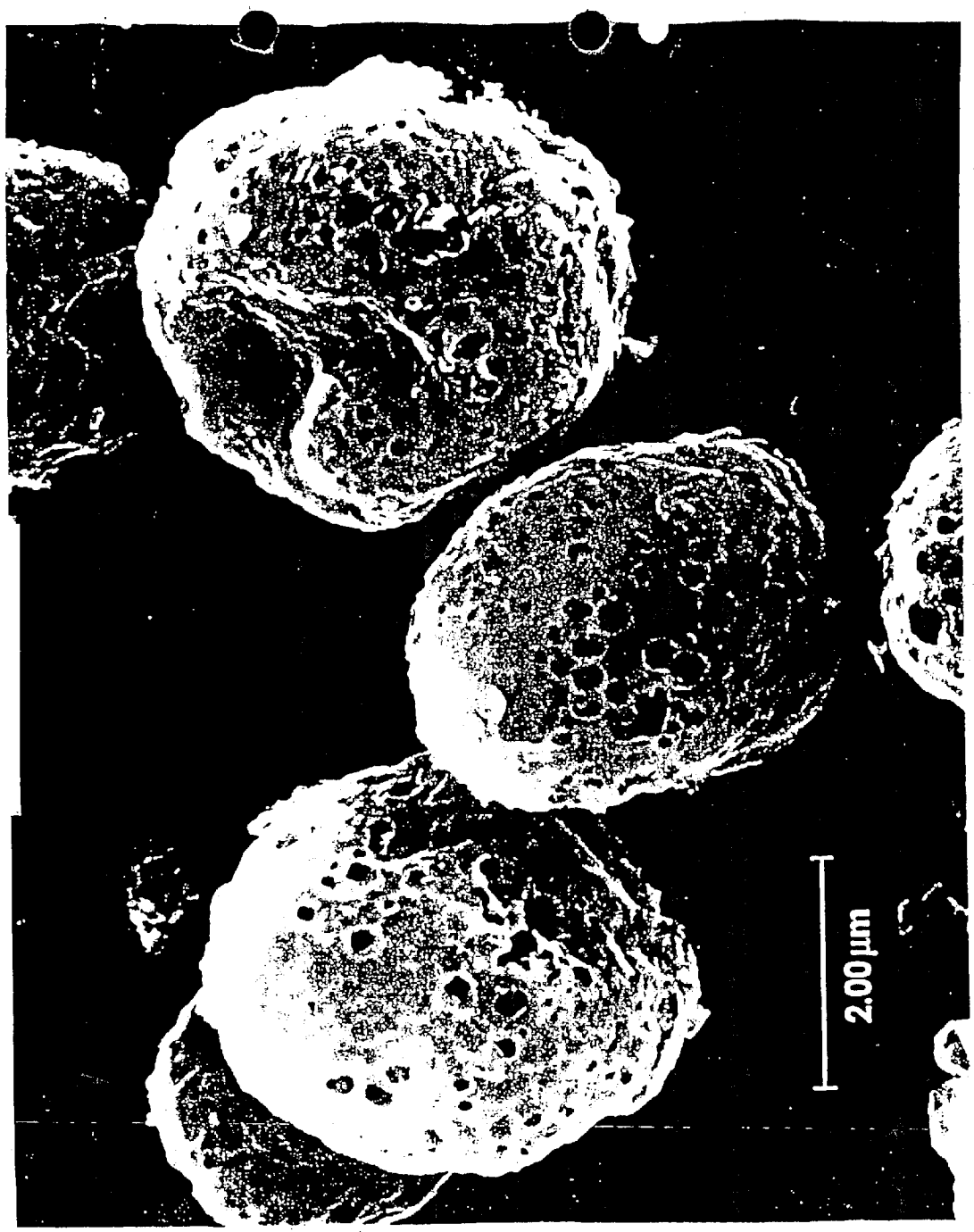

While the present invention may be embodied in many different forms, disclosed herein are specific illustrative embodiments thereof that exemplify the principles of the invention. It should be emphasized that, the present invention is not limited to the specific embodiments illustrated.

As set forth above, the present invention provides systems, methods and compositions that allow for the formation and administration of stabilized suspensions or dispersions, having a nonaqeous continuous phase, that may advantageously be used for the pulmonary delivery of bioactive agents in conjunction with a nebulizer. In this regard, it will be appreciated that the stabilized dispersions may comprise any colloidal system, including, reverse emulsions, microemulsions or particulate (i.e. non-liquid particles) dispersions that may be nebulized to effectively deliver a bioactive agent to the pulmonary air passages of a patient. Particularly preferred embodiments comprise stabilized dispersions incorporating a liquid fluorochemical continuous phase or suspension medium. In any event, the stabilized dispersion will preferably be administered to the pulmonary air passages of a patient using a nebulizer (e.g. a single- bolus type nebulizer).

Traditional prior art nebulizer preparations typically comprise aqueous solutions of the selected pharmaceutical compound. With such prior art nebulizer preparations, it has long been established that corruption of the incorporated therapeutic compound can severely reduce efficacy. For example, with conventional aqueous multi-dose nebulizer preparations, bacterial contamination is a constant problem. In addition, the solubilized medicament may precipitate out, or degrade over time, adversely affecting the delivery profile. This is particularly true of larger, more labile biopolymers such as enzymes or other types of proteins. Precipitation of the incorporated bioactive agent may lead to particle growth that results in a substantial reduction in lung penetration and a corresponding decrease in bioavailability. Such dosing incongruities markedly decrease the effectiveness of any treatment.

The present invention overcomes these and other difficulties by providing stabilized dispersions with a nonaqueous continuous phase that preferably comprises a fluorinated compound (i.e. a fluorochemical, fluorocarbon or perfluorocarbon). Particularly preferred embodiments of the present invention comprise fluorochemicals that are liquid at room temperature. As indicated above, the use of such compounds, whether as a continuous phase or, as a suspension medium, provides several advantages over prior art liquid inhalation preparations. In this regard, it is well established that many fluorochemicals have a proven history of safety and biocompatibility in the lung. Further, in contrast to aqueous solutions, fluorochemicals do not negatively impact gas exchange following pulmonary administration. To the contrary, they may actually be able to improve gas exchange and, due to their unique wettability characteristics, are able to carry an aerosolized stream of particles deeper into the lung, thereby improving systemic delivery of the desired pharmaceutical compound. In addition, the relatively non-reactive nature of fluorochemicals acts to retard any degradation of an incorporated bioactive agent. Finally, many fluorochemicals are also bacteriostatic thereby decreasing the potential for microbial growth in compatible nebulizer devices.

As previously indicated, the present invention may comprise any one of a number of colloidal systems including, but not limited to, reverse emulsions, microemulsions and particulate dispersions. For the purposes of the instant application the terms shall be used in accordance with their common meanings unless otherwise dictated by contextual constraints. Thus, those skilled in the art will appreciate that emulsions (whether micro, or reverse [water-in-oil]) will comprise a dispersion of liquid particulates in a liquid continuous phase. Conversely, a particulate suspension or dispersion shall, as used herein, be held to comprise a distribution of non-liquid particles in a liquid continuous phase or suspension medium.

While inhalation preparations compatible with the present invention may comprise any colloidal system that is capable of nebulization or aerosolization the following discussion, for the purpose of explanation, will largely be directed to particularly preferred embodiments of the present invention comprising stabilized particulate dispersions. It should be emphasized that, the scope and content of (he present invention is not limited to these specific illustrative embodiments and, in particular, is not limited to those embodiments comprising particulate dispersions. While such dispersions are particularly effective in terms of stability and pulmonary distribution, nebulized reverse emulsions may also provide for the efficient pulmonary delivery of bioactive compounds. As such, their use is specifically contemplated as being within the scope of the present invention.

With regard to particulate dispersions, the enhanced stability provided by the suspensions of the present invention may be achieved by lowering the van der Waals attractive forces between the suspended particles, and by reducing the differences in density between the suspension medium and the particles. In accordance with the teachings herein, the increases in suspension stability may be imparted by engineering perforated microstructures that are then dispersed in a compatible suspension medium. In this respect, the perforated microstructures comprise pores, voids, hollows, defects or other interstitial spaces that allow the fluid suspension medium to freely permeate or perfuse the particulate boundary. Particularly preferred embodiments comprise perforated microstructures that are both hollow and porous, almost honeycombed or foam-like in appearance. In especially preferred embodiments the perforated microstructures comprise hollow, porous spray dried microspheres.

When perforated microstructures are placed in the suspension medium, the suspension medium is able to permeate the particles, thereby creating a "homodispersion", wherein both the continuous and dispersed phases are essentially indistinguishable. Since the defined or "virtual" particles (i.e. comprising the volume circumscribed by the microstructure matrix) are made up almost entirely of the medium in which they are suspended, the forces driving particle aggregation (flocculation) are minimized. Additionally, the differences in density between the defined or virtual particles and the continuous phase are minimized by having the microstructures filled with the medium, thereby effectively slowing particle creaming or sedimentation. As such, the stabilized suspensions of the present invention are particularly compatible with inhalation therapies and may be used in conjunction with metered dose inhalers (MDIs), dry-powder inhalers, and nebulizers.

More specifically, the particulate suspensions of the present invention may be designed to decrease the attractive forces between particles. The principal forces driving flocculation in nonaqueous media are van der Waals attractive forces. Van der Waals forces are quantum mechanical in origin, and can be visualized as attractions between fluctuating dipoles (i.e. induced dipole-induced dipole interaction). Dispersion forces are extremely short-range and scale as the sixth power of the distance between atoms. When two macroscopic bodies approach one another, the dispersion attractions between the atoms sum up. The resulting force is of considerably longer range, and depends on the geometry of the interacting bodies.

More specifically, for two spherical particles, the magnitude of the van der Waals potential, $V_A$, can be approximated by:

$$V_A = \frac{-A_{\it{eff}}}{6H_0} \frac{R_1 R_2}{(R_1 + R_2)},$$

where $A_{\it{eff}}$ is the effective Hamaker constant which accounts for the nature of the particles and the medium, $H_0$ is the distance between particles, and $R_1$ and $R_2$ are the radii of spherical particles 1 and 2. The effective Hamaker constant is proportional to the difference in the polarizabilities of the dispersed particles and the suspension medium: $A_{\it{eff}}=(\sqrt{A_{SM}}-\sqrt{A_{PART}})^2$, where $A_{SM}$ and $A_{PART}$ are the Hamaker constants for the suspension medium and the particles, respectively. As the suspended particles and the dispersion medium become similar in nature, $A_{SM}$ and $A_{PART}$ become closer in magnitude, and $A_{eff}$ and $V_A$ become smaller. That is, by reducing the differences between the Hamaker constant associated with suspension medium and the Hamaker constant associated with the dispersed particles, the effective Hamaker constant (and corresponding van der Waals attractive forces) may be reduced.

One way to minimize the differences in the Hamaker constants is to create a "homodispersion", that is make both the continuous and dispersed phases essentially indistinguishable as discussed above. In addition to exploiting the morphology of the particles to reduce the effective Hamaker constant, the components of the structural matrix (defining the perforated microstructures) will preferably be chosen so as to exhibit a Hamaker constant relatively close to that of the selected suspension medium. In this respect, one may use the actual values of the Hamaker constants of the suspension medium and the particulate components to determine the compatibility of the dispersion ingredients and to provide a good indication as to the stability of the preparation. Alternatively, one could select relatively compatible perforated microstructure components and suspension mediums using readily discernible characteristic physical values that coincide with measurable Hamaker constants.

In this respect, it has been found that the refractive index values of many compounds tend to scale with the corresponding Hamaker constant. Accordingly, easily measurable refractive index values may be used to provide a fairly good indication as to which combination of suspension medium and particle excipients will provide a dispersion having a relatively low effective Hamaker constant and associated stability. It will be appreciated that, since refractive indices of compounds are widely. available or easily derived, the use of such values allows for the formation of stabilized dispersions in accordance with the present invention without undue experimentation. For the purpose of illustration only, the refractive indices of several compounds compatible with the disclosed dispersions are provided in Table I immediately below:

TABLE I

| Compound | Refractive Index |
| --- | --- |
| HFA-134a | 1.172 |
| HFA-227 | 1.223 |
| CFC-12 | 1.287 |
| CFC-114 | 1.288 |
| PFOB | 1.305 |
| Mannitol | 1.333 |
| Ethanol | 1.361 |
| n-octane | 1.397 |
| DMPC | 1.43 |
| Pluronic F-68 | 1.43 |
| Sucrose | 1.538 |
| Hydroxyethylstarch | 1.54 |
| Sodium chloride | 1.544 |

Consistent with the compatible dispersion components set forth above, those skilled in the art will appreciate that the formation of dispersions wherein the components have a refractive index differential of less than about 0.5 is preferred. That is, the refractive index of the suspension medium will preferably be within about 0.5 of the refractive index associated with the suspended particles or perforated microstructures. It will further be appreciated that, the refractive index of the suspension medium and the particles may be measured directly or approximated using the refractive indices of the major component in each respective phase. For the particles or perforated microstructures, the major component may be determined on a weight percent basis. For the suspension medium, the major component will typically be derived on a volume percentage basis. In selected embodiments of the present invention, the refractive index differential value will preferably be less than about 0.45, about 0.4, about 0.35 or even less than about 0.3. Given that lower refractive index differentials imply greater dispersion stability, particularly preferred embodiments comprise index differentials of less than about 0.28, about 0.25, about 0.2, about 0.15 or even less than about 0.1. It is submitted that a skilled artisan will be able to determine which dispersion components are particularly compatible without undue experimentation given the instant disclosure. The ultimate choice of preferred components will also be influenced by other factors, including biocompatibility, regulatory status, ease of manufacture and cost.

In contrast to prior art attempts to provide stabilized suspensions which require surfactants that are soluble in the suspension medium, the present invention may provide stabilized dispersions, at least in part, by immobilizing the bioactive agent(s) within the structural matrix of the hollow, porous microstructures. Accordingly, preferred excipients useful in the present invention are substantially insoluble in the suspension medium. Under Such conditions, even surfactants like, for example, lecithin cannot be considered to have surfactant properties in the present invention since surfactant performance requires the amphiphile to be reasonably soluble in the suspension medium. The use of insoluble excipients also reduces the potential for particle growth by Ostwald ripening.

As discussed above, the minimization of density differences between the particles and the continuous phase may be improved by the perforated and/or hollow nature of incorporated microstructures, such that the suspension medium constitutes most of the particle volume. As used herein, the term "particle volume" corresponds to the volume of suspension medium that would be displaced by the incorporated hollow/porous particles if they were solid, i.e. the volume defined by the particle boundary. For the purposes of explanation these fluid filled particulate volumes may be referred to as "virtual particles." Preferably, the average volume of the bioactive agent and/or excipient shell or matrix (i.e. the volume of medium actually displaced by the perforated microstructure) comprises less than 70% of the average particle volume (or less. than 70% of the virtual particle). More preferably, the volume of the microparticulate matrix comprises less than about 50%, 40%, 30% or even 20% of the average particle volume. Even more preferably, the average volume of the shell/matrix comprises less than about 10%, 5% or 3% of the average particle volume. Those skilled in the art will appreciate that such matrix, or shell volumes typically contribute little to the virtual particle density that is overwhelmingly dictated by the suspension medium found therein. Of course, in selected embodiments the excipients or bioactive agents used to form the perforated microstructure may be chosen so the density of the resulting matrix or shell approximates the density of the surrounding suspension medium.

It will be appreciated that, the use of such microstructures will allow the apparent density of the virtual particles to approach that of the suspension medium. Moreover, as previously discussed, the components of the microparticulate matrix are preferably selected, as much as possible given other considerations, to approximate the density of suspension medium. Accordingly, in preferred embodiments of the present invention the virtual particles and the suspension medium will have a density differential of less than about 0.6 g/cm$^3$. That is, the mean density of the virtual particles (as defined by the matrix boundary) will be within approximately 0.6 g/cm$^3$ of the suspension medium. More preferably, the mean density of the virtual particles will be within 0.5, 0.4, 0.3 or 0.2 g/cm$^3$ of the selected suspension medium. In even more preferable embodiments the density differential will be less than about 0.1, 0.05, 0.01, or even less than 0.005 g/cm$^3$.

In addition to the aforementioned advantages, the use of hollow, porous particles allows for the formation of free-flowing dispersions comprising much higher volume fractions of particles in suspension. It should be appreciated that, the formulation of prior art dispersions at volume fractions approaching close-packing generally results in dramatic increases in dispersion viscoelastic behavior. Rheological behavior of this type is not appropriate for inhalation applications. Those skilled in the art will appreciate that, the volume fraction of the particles may be defined as the ratio of the apparent volume of the particles (i.e. the particle volume) to the total volume of the system. Each system has a maximum volume fraction or packing fraction. For example, particles in a simple cubic arrangement reach a maximum packing fraction of 0.52, while those in a face centered cubic/hexagonal close packed configuration reach a maximum packing fraction of approximately 0.74. For non-spherical particles or polydisperse systems, the derived values are different. Accordingly, the maximum packing fraction is often considered to be an empirical parameter for a given system.

Here, it was surprisingly found that, the use of porous structures in the present invention did not introduce undesirable viscoelastic behavior even at high volume fractions approaching close packing. To the contrary, they remain as free flowing, low viscosity suspensions having little or no yield stress when compared with analogous suspensions comprising solid particulates. The low viscosity of disclosed preferred suspensions is thought to be due, at least in large part, to the relatively low van der Waals attraction between the fluid-filled hollow, porous particles. As such, in selected embodiments the volume fraction of the disclosed dispersions is greater than approximately 0.3. Other embodiments may have packing values on the order of 0.3 to about 0.5 or, on the order of 0.5 to about 0.8, with the higher values approaching a close packing condition. Moreover, as particle sedimentation tends to naturally decrease when the volume fraction approaches close packing, the formation of relatively concentrated dispersions may further increase formulation stability.

Although the methods and compositions of the present invention may be used to form relatively concentrated suspensions, the stabilizing factors work equally well at much lower packing volumes and, such dispersions are contemplated as being within the scope of the instant disclosure. In this regard, it will be appreciated that dispersions comprising low volume fractions are extremely difficult to stabilize using prior art techniques. Conversely, dispersions incorporating perforated microstructures comprising a bioactive agent as described herein are particularly stable even at low volume fractions. Accordingly, the present invention allows for stabilized dispersions, and particularly respiratory dispersions, to be formed and used, at volume fractions less than 0.3. In some preferred embodiments, the volume fraction is approximately 0.0001–0.3, or more preferably 0.001–0.01. Yet other preferred embodiments comprise stabilized suspensions having volume fractions from approximately 0.01. to approximately 0.1.

In other preferred embodiments, perforated microstructures may be used to stabilize dilute suspensions of micronized bioactive agents. In such embodiments the perforated microstructures may be added to increase the volume fraction of particles in the suspension, thereby increasing suspension stability with respect to creaming or sedimentation. Further, in these embodiments, the incorporated microstructures may also act in preventing close approach (aggregation) of micronized drug particles. It should be appreciated that, the perforated microstructures incorporated in such embodiments do not necessarily comprise a bioactive agent. Rather, they may be formed exclusively of various excipients, including surfactants.

Of course, it will also be appreciated that the stabilized dispersions of the present invention may comprise relatively solid or non-perforated particulates without the addition of perforated microstructures. That is, depending on the size, composition and density of the suspended microparticulates, as well as the selection of suspension medium, effective particulate dispersions for nebulization may be formed using relatively non-porous or micronized particulates. In a preferred embodiment, the suspended particulates may comprise nanocrystals such as. those disclosed in U.S. Pat. No. 5,667,809 which is incorporated herein by reference. As with embodiments comprising perforated microstructures, such preparations will preferably comprise a fluorochemical suspension medium. Accordingly, in a broad sense, the present invention provides for the formation and pulmonary administration of stabilized dispersions comprising relatively non-porous particulates (e.g. micronized particles), porous particulates (i.e. hollow porous microspheres or perforated microstructures) and combinations thereof.

While the stabilized dispersions may comprise particulates exhibiting various morphologies, particularly preferred embodiments of the present invention comprise a plurality of perforated microstructures or microparticulates that are dispersed, or suspended in the suspension medium. In such embodiments, the perforated microstructures comprise a structural matrix that exhibits, defines or comprises voids, pores, defects, hollows, spaces, interstitial spaces, apertures, perforations or holes that allows the surrounding suspension medium to freely permeate, fill or pervade the microstructure. The absolute shape (as opposed to the morphology) of the perforated microstructure is generally not critical and, any overall configuration that provides the desired stabilization characteristics is contemplated as being within the scope of the invention. Accordingly, while preferred embodiments incorporating perforated microstructures can comprise approximately microspherical shapes, collapsed, deformed or fractured particulates are also compatible. With that caveat, it will be appreciated that particularly preferred embodiments of the invention comprise spray dried hollow, porous microspheres.

In order to maximize dispersion stability and optimize distribution upon administration, the mean geometric particle size of the perforated microstructures is preferably about 0.5–50 $\mu$m, more preferably 1–30 $\mu$m. It will be appreciated that, large particles (i.e. greater than 50 $\mu$m) should not be used as large particles may tend to aggregate or, separate from the suspension and not be effectively nebulized. In especially preferred embodiments, the mean geometric particle size (or diameter) of the perforated microstructures is less than 20 $\mu$m or less than 10 $\mu$m. More preferably, the mean geometric diameter is less than about 5 $\mu$m. In especially preferred embodiments, the perforated microstructures will comprise a powder of dry, hollow, porous microspherical shells of approximately 1 to 10 $\mu$m in diameter, with shell thicknesses of approximately 0.1 μm to approximately 0.5 μm. It is a particular advantage of the present invention that, the particulate concentration of the dispersions and structural matrix components can be adjusted to optimize the delivery characteristics of the selected particle size.

As indicated throughout the instant specification, the dispersions of the present invention are preferably stabilized. In a broad sense, the term "stabilized dispersion" will be held to mean any dispersion that resists aggregation, flocculation or creaming to the extent required to provide for the effective delivery of a bioactive agent. While those skilled in the art will appreciate that there are several methods that may be used to assess the stability of a given dispersion, a preferred method for the purposes of the present invention comprises determination of creaming or sedimentation time. In this regard, the creaming time shall be defined as the time for the suspended drug particulates to cream to ½ the volume of the suspension medium. Similarly, the sedimentation time may be defined as the time it takes for the particulates to sediment in ½ the volume of the liquid medium. One relatively simple way to determine the creaming time of a preparation is to provide the particulate suspension in a sealed glass vial. The vials are agitated or shaken to provide relatively homogeneous dispersions which are then set aside and observed using appropriate instrumentation or by visual inspection. The time necessary for the suspended particulates to cream to ½ the volume of the suspension medium (i.e., to rise to the top half of the suspension medium), or to sediment within 1/12 the volume (i.e:, to settle in the bottom ½ of the medium), is then noted. Suspension formulations having a creaming time greater than 1 minute are preferred and indicate suitable stability. More preferably, the stabilized dispersions comprise creaming times of greater than about 2, 5, 10, 15, 20 or 30 minutes. In particularly preferred embodiments, the stabilized dispersions exhibit creaming times of greater than about 1, 1.5, 2, 2.5, 3, 4 or even 5 hours. Substantially equivalent periods for sedimentation times are indicative of compatible dispersions.

With respect to the preparations of the present invention, the porosity of incorporated microstructures may contribute significantly to establishing dispersion stability. In this respect, the mean porosity of the perforated microstructures may be determined through electron microscopy coupled with modem imaging techniques. More specifically, electron micrographs of representative samples of the perforated microstructures may be obtained and digitally analyzed to quantify the porosity of the preparation. Such methodology is well known in the art and, may be undertaken without undue experimentation.

For the purposes of the present invention, the mean porosity (i.e. the percentage of the particle surface area that is open to the interior and/or a central void) of the perforated microstructures may range from approximately 0.5% to approximately 80%. In more preferred embodiments, the mean porosity will range from approximately 2% to approximately 40%. Based on selected production parameters, the mean porosity may be greater than approximately, 2%, 5%, 10%, 15%, 20%, 25% or 30% of the microstructure surface area. In other embodiments, the mean porosity of the microstructures may be greater than about 40%, 50%, 60%, 70% or even 80%. As to the pores themselves, they typically range in size from about 5 nm to about 400 nm, with mean pore sizes preferably in the range of from about 20 nm to about 200 nm. In particularly preferred embodiments the mean pore size will be in the range of from about 50 nm to about 100 nm. As may be seen in FIGS. 1A1 to 1F2, and discussed in more detail below, it is a significant advantage of the present invention that the pore size, and porosity, may be closely controlled by careful selection of the incorporated components and production parameters.

Along with the geometric configuration, the perforated or porous and/or hollow design of microstructures can also play an important role in the resulting aerosol properties during nebulization. In this respect, the perforated structure, and relatively high surface area of the dispersed microparticles, enables them to be carried along in the aerosol cloud during inhalation with greater ease and, for longer distances, than non-perforated particles of comparable size. Because of their high porosity, the density of the particles is significantly less than 1.0 g/cm$^3$, typically less than 0.5 g/cm$^3$, more often on the order of 0.1 g/cm$^3$, and as low as 0.01 g/cm$^3$. Unlike the geometric particle size, the aerodynamic particle size, $d_{aer}$, of the perforated microstructures depends substantially on the particle density, ρ: $d_{aer} = d_{geo}\rho$, where $d_{geo}$ is the geometric diameter. For a particle density of 0.1 g/cm$^3$, $d_{aer}$ will be roughly three times smaller than $d_{geo}$, leading to increased particle deposition into the peripheral regions of the lung and correspondingly less deposition in the throat. In this regard, the mean aerodynamic diameter of the perforated microstructures is preferably less than about 5 μm, more preferably less than about 3 μm, and, in particularly preferred embodiments, less than about 2 μm. Such particle distributions will act to increase the deep lung deposition of the administered agent.

As will be shown subsequently in the Examples, the particle size distribution of the aerosol formulations of the present invention are measurable by conventional techniques such as cascade impaction, or by time of flight analytical methods. Determination of the emitted dose in nebulized inhalations was done according to the proposed U.S. Pharmacopoeia method (*Pharmacopeial Previews,* 22(1996) 3065) which is incorporated herein by reference. These and related techniques enable the "fine particle fraction" of the nebulized aerosol, which corresponds to those particulates that are likely to effectively deposited in the lung, to be calculated. As used herein, the phrase "fine particle fraction" refers to the percentage of the total amount of active medicament delivered per actuation from the mouthpiece onto plates 2–7 of an 8 stage Andersen cascade impactor. Based on such measurements, the formulations of the present invention will preferably have a fine particle fraction for local airway delivery of approximately 20% or more, by weight of the perforated microstructures (w/w). More preferably, they will exhibit a fine particle fraction of from about 25% to 80% w/w, and even more preferably from about 30 to 70% w/w. In selected embodiments the present invention will preferably comprise a fine particle fraction of greater than about 30%, 40%, 50%, 60%, 70% or 80% by weight. For systemic delivery, the fine particle fraction will preferably be greater than 80% by weight, more preferably, greater than 90% by weight.

Whatever configuration and/or size distribution is ultimately selected for the incorporated particulate (whether a perforated microstructure or relatively solid non-porous particulate), the composition thereof may comprise any one of a number of biocompatible materials. With regard to perforated microstructures, it will be appreciated that, as used herein, the terms "structural matrix" or "microstructure matrix" are equivalent and shall be held to mean any solid material forming the perforated microstructures which define a plurality of voids, apertures, hollows, defects, pores, holes, fissures, etc. that promote the formation of stabilized dispersions as explained above. The structural matrix may be soluble or insoluble in an aqueous environment. In preferred embodiments the perforated microstructure defined by the structural matrix comprises a spray dried hollow porous microsphere incorporating at least one surfactant. For other selected embodiments, the particulate material may be coated one or more times with polymers, surfactants or other compounds which aid suspension.

More generally, particulates useful in the stabilized dispersions of the present invention may be formed of any biocompatible material that is relatively stable and preferably insoluble with respect to the selected suspension medium. While a wide variety of materials may be used to form the particles, in particularly preferred embodiments, the particles (or structural matrix) is associated with, or comprises, a surfactant such as phospholipid or fluorinated surfactant. Although not required, incorporation of a compatible surfactant can improve the stability of the respiratory dispersions, increase pulmonary deposition and facilitate the preparation of the suspension. Moreover, by altering the components, the density of the particle or structural matrix may be adjusted to approximate the density of the surrounding medium and further stabilize the dispersion. Finally, as will be discussed in further detail below, perforated microstructures preferably comprise at least one bioactive agent.

As set forth above, the relatively non-porous particles or perforated microstructures of the present invention, may optionally be associated with, or comprise, one or more surfactants. Moreover, miscible surfactants may optionally be combined with the suspension medium liquid phase. It will be appreciated by those skilled in the art that, the use of surfactants, while not necessary to practice the instant invention, may further increase dispersion stability, simplify formulation procedures or increase bioavailability upon administration. Of course combinations of surfactants, including the use of one or more in the liquid phase and one or more associated with the perforated microstructures are contemplated as being within the scope of the invention. By "associated with or comprise" it is meant that the particle or perforated microstructure may incorporate, adsorb, absorb, be coated with or be formed by the surfactant.

In a broad sense, surfactants suitable for use in the present invention include any compound or composition that aids in the formation and maintenance of the stabilized respiratory dispersions by forming a layer at the interface between the particle and the suspension medium. The surfactant may comprise a single compound or any combination of compounds, such as in the case of co-surfactants. Particularly preferred surfactants are substantially insoluble in the medium, nonfluorinated, and selected from the group consisting of saturated and unsaturated lipids, nonionic detergents, nonionic block copolymers, ionic surfactants, and combinations of such agents. It should be emphasized that, in addition to the aforementioned surfactants, suitable (i.e. biocompatible) fluorinated surfactants are compatible with the teachings herein and may be used to provide the desired stabilized preparations.

Lipids, including phospholipids, from both natural and synthetic sources are particularly compatible with the present invention and may be used in varying concentrations to form the particle or structural matrix. Generally compatible lipids comprise those that have a gel to liquid crystal phase transition greater than about 40° C. Preferably, the incorporated lipids are relatively long chain (i.e. $C_{16}$–$C_{22}$) saturated lipids and more preferably comprise phospholipids. Exemplary phospholipids useful in the disclosed stabilized preparations comprise egg phosphatidylcholine, dilauroylphosphatidylcholine, dioleylphosphatidylcholine, dipalmitoylphosphatidyl-choline, disteroylphosphatidylcholine, short-chain phosphatidylcholines, phosphatidylethanolamine, dioleylphosphatidylethanolamine, phosphatidylserine, phosphatidylglycerol, phosphatidylinositol, glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate. Due to their excellent biocompatibility characteristics, phospholipids and combinations of phospholipids and poloxamers are particularly suitable for use in the stabilized dispersions disclosed herein.

Compatible nonionic detergents comprise: sorbitan esters including sorbitan trioleate (Span® 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.) which is incorporated herein in its entirety. Preferred block copolymers include diblock and triblock copolymers of polyoxyethylene and polyoxypropylene, including poloxamer 188 (Pluronic® F-68), poloxamer 407 (Pluronic® F-127), and poloxamer 338. Ionic surfactants such as sodium sulfosuccinate, and fatty acid soaps may also be utilized. In preferred embodiments the microstructures may comprise oleic acid or its alkali salt.

In addition to the aforementioned surfactants, cationic surfactants or lipids are preferred especially in the case of delivery or RNA or DNA. Examples of suitable cationic lipids include: cetylpyridinium chloride, DOTMA, N-[1-(2,3-dioleyloxy)propyl]-N,N,N-trimethylammonium chloride; DOTAP, 1,2-dioleyloxy-3-(trimethylammonio)propane; and DOTB, 1,2-dioleyl-3-(4'-trimethylammonio) butanoyl-sn-glycerol. Polycationic amino acids such as polylysine, and polyarginine are also contemplated.

Those skilled in the art will further appreciate that, a wide range of surfactants, including those not listed above, may optionally be used in conjunction with the present invention. Moreover, the optimum surfactant, or combination thereof, for a given application can readily be determined by empirical studies that do not require undue experimentation. It will further be appreciated that, the preferred insolubility of any incorporated surfactant in the suspension medium will dramatically decrease the associated surface activity. As such, it is arguable as to whether these materials have surfactant-like character prior to contracting an aqueous bioactive surface (e.g. the aqueous hypophase in the lung). Finally, as discussed in more detail below, surfactants comprising the porous particles may also be useful in the formation of precursor oil-in-water emulsions (i.e. spray drying feed stock) used during processing to form the structural matrix or bioactive particulate.

Unlike prior art formulations, it has surprisingly been found that the incorporation of relatively high levels of surfactants (i.e. phospholipids) may be used to increase the stability of the disclosed dispersions. That is, on a weight to weight basis, the structural matrix of the perforated microstructures may comprise relatively high levels of surfactant.

In this regard, the perforated microstructures will preferably comprise greater than about 1%, 5%, 10%, 15%, 18%, or even 20% w/w surfactant. More preferably, the perforated microstructures will comprise greater than about 25%, 30%, 35%, 40%, 45%, or 50% w/w surfactant. Still other exemplary embodiments will comprise perforated microstructures wherein the surfactant or surfactants are present at greater than about 55%, 60%, 65%, 70%, 75%, 80%, 85%, 90% or even 95% w/w. In selected embodiments the perforated microstructures will comprise essentially 100% w/w of a surfactant such as a phospholipid. Those skilled in the art will appreciate that, in such cases, the balance of the structural matrix (where applicable) will likely comprise a bioactive agent(s) or non surface active excipient(s) or additive(s).

As previously indicated, stabilized dispersions comprising perforated microstructures merely represent a preferred embodiment of the present invention. Accordingly, while such surfactant levels are preferably employed in perforated microstructures, equivalent surfactant levels may also be used to provide stabilized systems comprising relatively nonporous, or substantially solid, particulates. That is, while preferred embodiments will comprise perforated microstructures or microspheres associated with high levels of surfactant, acceptable dispersions may be formed using relatively low or non-porous particulates (e.g. micronized particulates) of the same surfactant concentration. In this respect such embodiments are specifically contemplated as being within the scope of the present invention.

In other preferred embodiments, relatively non-porous particles or the structural matrix defining the perforated microstructures optionally comprises synthetic or natural polymers or combinations thereof. In this respect useful polymers comprise polylactides, polylactideglycolides, cyclodextrins, polyacrylates, methylcellulose, carboxymethylcellulose, polyvinyl alcohols, polyanhydrides, polylactons, polyvinyl pyrrolidones, polysaccharides (dextrans, starches, chitin, chitosan, etc.), hyaluronic acid, proteins, (albumin, collagen, gelatin, etc.). Those skilled in the art will appreciate that, by selecting the appropriate polymers, the delivery profile of the respiratory dispersion may be tailored to optimize the effectiveness of the bioactive agent.

In addition to the aforementioned polymer materials and surfactants, it may be desirable to add other excipients to an inhalation formulation to improve microsphere (or non-porous particulate) rigidity, drug delivery and deposition, shelf-life and patient acceptance. Such optional excipients include, but are not limited to: coloring agents, taste masking agents, buffers, hygroscopic agents, antioxidants, and chemical stabilizers. Further, excipients may be incorporated in, or added to, the particles or particulate matrix to provide structure and form to the perforated microstructures (i.e. microspheres). Such excipients may include, but are not limited to, carbohydrates including monosaccharides, disaccharides and polysaccharides. For example, monosaccharides such as dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (hydroxyethylstarch), cyclodextrins and maltodextrins. Amino acids are also suitable excipients with glycine preferred. Mixtures of carbohydrates and amino acids are further held to be within the scope of the present invention. The inclusion of both inorganic (e.g. sodium. chloride, calcium chloride), organic salts (e.g. sodium citrate, sodium ascorbate, magnesium gluconate, sodium gluconate, tromethamine hydrochloride) and buffers is also contemplated. Of course, it will be appreciated that, the selected excipients may be added to the dispersion as separate particles or perforated microstructures.

Yet other preferred embodiments include non-porous particles or perforated microstructures that may comprise, or may be coated with, charged species that prolong residence time at the point of contact or enhance penetration through mucosae. For example, anionic charges are known to favor mucoadhesion while cationic charges may be used to associate the formed microparticulate with negatively charged bioactive agents such as genetic material. The charges may be imparted through the association or incorporation of polyanionic or polycationic materials such as polyacrylic acids, polylysine, polylactic acid and chitosan.

In addition to, or instead of, the components discussed above, the particles, perforated microstructures or aqueous emulsion droplets will preferably comprise at least one bioactive agent. As used herein, "bioactive agent" refers to a substance which is used in connection with an application that is therapeutic or diagnostic in nature, such as in methods for diagnosing the presence or absence of a disease in a patient and/or in methods for treating a disease in a patient. Particularly preferred bioactive agents for use in accordance with the invention include antiallergics, peptides and proteins, bronchodilators and anti-inflammatory steroids for use in the treatment of respiratory disorders such as asthma by inhalation therapy.

It will be appreciated that, the distributed particles or perforated microstructures of the present invention may exclusively comprise one or more bioactive agents (i.e. 100% w/w). However, in selected embodiments the particles or perforated microstructures may incorporate much less bioactive agent depending on the activity thereof. Accordingly, for highly active materials, the particles may incorporate as little as 0.001% by weight, although a concentration of greater than about 0.1% w/w is preferred. Other embodiments of the invention may comprise greater than about 5%, 10%, 15%, 20%, 25%, 30% or, even 40% W/w bioactive. agent. Still more preferably, the particles or perforated microstructures may comprise greater than about 50%, 60%, 70%, 75%, 80% or, even 90% w/w bioactive agent. In particularly preferred embodiments, the final stabilized respiratory dispersion desirably contains from about 40%–60% w/w, more preferably 50%–70% w/w, and even more preferably, 60%–90% w/w of bioactive agent relative to the weight of the microparticulate matrix or particulate. The precise amount of bioactive agent incorporated in the stabilized dispersions of the present invention is dependent upon the agent of choice, the required dose, and the form of the drug actually used for incorporation. Those skilled in the art will appreciate that, such determinations may be made by using well-known pharmacological techniques, in combination with the teachings of the present invention.

Accordingly, bioactive agents that may be administered in the form of aerosolized medicaments in conjunction with the teachings herein include any drug that may be presented in a form which is subject to pulmonary uptake in physiologically effective amounts. In selected embodiments (e.g. particulate dispersions), the incorporated agent will preferably be relatively insoluble in the suspension medium. In other embodiments, such as reverse emulsions, the selected agent may be substantially soluble in the disperse phase. Particularly preferred embodiments comprising a reverse emulsion will preferably comprise a hydrophilic bioactive agent.

In any case, compatible bioactive agents may comprise hydrophilic and lipophilic. respiratory agents, bronchodilators, antibiotics, antivirals, anti-inflammatories, steroids, antihistaminics, histamine antagonists, leukotriene inhibitors or antagonists, anticholinergics, antineoplastics, anesthetics, enzymes, lung surfactants, cardiovascular agents, genetic material including DNA and RNA, viral vectors, immunoactive agents, imaging agents, vaccines, immunosuppressive agents, peptides, proteins and combinations thereof. Particularly preferred bioactive agents, for local administration using aerosolized medicaments in accordance with the present invention include, mast cell inhibitors (anti-allergics), bronchodilators, and anti-inflammatory steroids for use in the treatment of respiratory disorders such as asthma by inhalation therapy, for example cromoglycate (e.g. the sodium salt), and albuterol. (e.g. the sulfate salt). For systemic delivery (e.g. for the treatment of autoimmune diseases such as diabetes or multiple sclerosis), peptides and proteins are particularly preferred.

Exemplary. medicaments or bioactive agents may be selected from, for example, analgesics, e.g. codeine, dihydromorphine, ergotamine, fentanyl, or morphine; anginal preparations, e.g. diltiazem; mast cell inhibitors, e.g. cromolyn sodium; antiinfectives, e.g. cephalosporins, macrolides, quinolines, penicillins, streptomycin, sulphonamides, tetracyclines and pentamidine; antihistamines, e.g. methapyrilene; anti-inflammatories, e.g. fluticasone propionate, beclomethasone dipropionate, flunisolide, budesonide, tripedane, cortisone, prednisone, prednisilone, dexamethasone, betamethasone, or triamcinolone acetonide; antitussives, e.g. noscapine; bronchodilators, e.g. ephedrine, adrenaline, fenoterol, formoterol, isoprenaline, metaproterenol, salbutamol, albuterol, salmeterol, terbutaline; diuretics, e.g. amiloride; anticholinergics, e.g. ipatropium, atropine, or oxitropium; lung surfactants e.g. Surfaxin, Exosurf, Survanta; xanthines, e.g. aminophylline, theophylline, caffeine; therapeutic proteins and peptides, e.g. DNAse, insulin, glucagon, T-cell receptor agbnists or antagonists, LHRH, nafarelin, goserelin, leuprolide, interferon, rhu IL-1 receptor, macrophage activation factors such as lymphokines and muramyl dipeptides, opioid peptides and neuropeptides such as enkaphalins, endorphins, renin inhibitors, cholecystokinins, growth hormones, leukotriene inhibitors, α-antitrypsin, and the like. In addition, bioactive agents that comprise an RNA or DNA sequence, particularly those useful for gene therapy, genetic vaccination or tolerization or antisense applications, may be incorporated in the disclosed dispersions as described herein. Representative DNA plasmids include pCMVβ (available from Genzyme Corp, Framington, Mass.) and pCMV-β-gal (a CMV promotor linked to the *E. coli* Lac-Z gene, which codes for the enzyme β-galactosidase).

With respect to particulate dispersions, the selected bioactive agent(s) may be associated with, or incorporated in, the particles or perforated microstructures in any form that provides the desired efficacy and is compatible with the chosen production techniques. Similarly, the incorporated bioactive agent may be associated with the discontinuous phase of a reverse emulsion. As used herein, the terms "associate" or "associating" mean that the structural matrix, perforated microstructure, relatively non-porous particle or discontinuous phase may comprise, incorporate, adsorb, absorb, be coated with or be formed by the bioactive agent. Where appropriate, the medicaments may be used in the form of salts (e.g. alkali metal or amine salts or as acid addition salts), or as esters, or as solvates (hydrates). In this regard, the form of the bioactive agents may be selected to optimize the activity and/or stability of the medicament and/or, to minimize the solubility of the medicament in the suspension medium. It will further be appreciated that the aerosolized formulations according to the invention may, if desired, contain a combination of two or more active ingredients. The agents may be provided in combination in a single species of perforated microstructure or particle or individually in separate species that are combined in the suspension medium or continuous phase. For example, two or more bioactive agents may be incorporated in a single feed stock preparation and spray dried to provide a single microstructure species comprising a plurality of medicaments. Conversely, the individual medicaments could be added to separate stocks and spray dried separately to provide a plurality of microstructure species with different compositions. These individual species could be added to the medium in any desired proportion and placed in inhalation delivery systems as described below. Further, as briefly mentioned above, the perforated microstructures (with or without an associated medicament) may be combined with one or more conventionally micronized bioactive agents to provide the desired dispersion stability.

Based on the foregoing, it will be appreciated by those skilled in the art that a wide variety of bioactive agents may be incorporated in the disclosed stabilized dispersions. Accordingly, the list of preferred bioactive agents above is exemplary only and not intended to be limiting. It will also be appreciated by those skilled in the art that, the proper amount of bioactive agent and the timing of the dosages may be determined for the formulations in accordance with already-existing information and without undue experimentation.

As seen from the passages above, various components may be associated with, or incorporated in the discontinuous phase, perforated microstructures or particles of the present invention. Similarly, several techniques may be used to provide particulates having compatible physiochemical properties, morphology (i.e. a perforated configuration) and density. Among other methods, perforated microstructures or particles compatible with the instant invention may be formed by techniques including lyophilization, spray drying, multiple emulsion, micronization, or crystallization. In preferred embodiments, relatively non-porous particles may be produced using techniques such as micronization, crystallization or milling. It will further be appreciated that, the basic concepts of many of these techniques are well known in the prior art and would not, in view of the teachings herein, require undue experimentation to adapt them so as to provide the desired particulates.

While several procedures are generally compatible with the present invention, particularly preferred embodiments typically comprise particulates or perforated microstructures formed by spray drying. As is well known, spray drying is a one-step process that converts a liquid feed to a dried particulate form. With respect to pharmaceutical applications, it will be appreciated that spray drying has been used to provide powdered material for various administrative routes including inhalation. See, for example, M. Sacchetti and M. M. Van Oort in: Inhalation Aerosols: Physical and Biological Basis for Therapy, A. J. Hickey, ed. Marcel Dekkar, New York, 1996, which is incorporated herein by reference.

In general, spray drying consists of bringing together a highly dispersed liquid, and a sufficient volume of hot air to produce evaporation and drying of the liquid droplets. The preparation to be spray dried or feed (or feed stock) can be any solution, course suspension, slurry, colloidal dispersion, or paste that may be atomized using the selected spray drying apparatus. Typically, the feed is sprayed into a current of warm filtered air that evaporates the solvent and conveys the dried product to a collector. The spent air is then exhausted with the solvent. Those skilled in the art will appreciate that several different types of apparatus may be used to provide the desired product. For example, commercial spray dryers manufactured by Buchi Ltd. or Niro Corp. will effectively produce particles of desired size. It will further be appreciated that these spray dryers, and specifically their atomizers, may be modified or customized for specialized applications, i.e. the simultaneous spraying of two solutions using a double nozzle technique. More specifically, a water-in-oil emulsion can be atomized from one nozzle and, a solution containing an anti-adherent such as mannitol can be co-atomized from a second nozzle. In other cases it may be desirable to push the feed solution though a custom designed nozzle using a high pressure liquid chromatography (HPLC) pump. Provided that microstructures comprising the correct morphology and/or composition are produced, the choice of apparatus is not critical and would be apparent to the skilled artisan in view of the teachings herein.

While the resulting spray-dried powdered particles typically are approximately spherical in shape, nearly uniform in size and frequently are hollow, there may be some degree of irregularity in shape depending upon the incorporated medicament and the spray drying conditions. In many instances, the dispersion stability of spray-dried microspheres or particles appears to be more effective if an inflating agent (or blowing agent) is used in their production. Particularly preferred embodiments may comprise an emulsion with the inflating agent as the disperse or continuous phase (the other phase being aqueous in nature). The inflating agent is preferably dispersed with a surfactant solution, using, for instance, a commercially available microfluidizer at a pressure of about 5,000 to 15,000 psi. This process forms an emulsion, preferably stabilized by an incorporated surfactant, typically comprising submicron droplets of water immiscible blowing agent dispersed in an aqueous continuous phase. The formation of such dispersions using this, and other techniques, are common and well known to those in the art. The blowing agent is preferably a fluorinated compound (e.g. perfluorohexane, perfluorooctyl bromide, perfluorodecalin, perfluorobutyl ethane) which vaporizes during the spray-drying process, leaving behind generally hollow, porous aerodynamically light microspheres. As will be discussed in more detail below, other suitable blowing agents include chloroform, Freons, and hydrocarbons. Nitrogen gas and carbon dioxide are also contemplated as suitable blowing agents.

Although perforated microstructures are preferably formed using a blowing agent as described above, it will be appreciated that, in some instances, no additional blowing agent is required and an aqueous dispersion of the medicament and surfactant(s) are spray dried directly. In such cases, the formulation may be amenable to process conditions (e.g., elevated temperatures) that generally lead to the formation of hollow, relatively porous microparticles. Moreover, the medicament may possess special physicochemical properties (e.g., high crystallinity, elevated melting temperature, surface activity, etc.) that make it particularly suitable for use in such techniques.

When a blowing agent is employed, the degree of porosity of the perforated microstructure appears to depend, at least in part, on the nature of the blowing agent, its concentration in the feed stock (i.e. as an emulsion), and the spray drying conditions. With respect to controlling porosity, it has surprisingly been found that the use of compounds, heretofore unappreciated as blowing agents, may provide particulates or perforated microstructures having particularly desirable characteristics. More particularly, in this novel and unexpected aspect of the present invention, it has been found that the use of fluorinated compounds having relatively high boiling points (i.e. greater than about 60° C.) may be used to produce particulates that are especially suitable for inhalation therapies. In this regard, it is possible to use fluorinated blowing agents having boiling points of greater than about 70° C., 80° C., 90° C. or even 95° C. Particularly preferred blowing agents have boiling points greater than the boiling point of water, i.e. greater than 100° C. (e.g. perflubron, perfluorodecalin). In addition, blowing agents with relatively low water solubility ($<10^{-6}$ M) are preferred since they enable the production of stable emulsion dispersions with mean weighted particle diameters less than 0.3 $\mu$m. As indicated above, these blowing agents will preferably be incorporated in an emulsified feed stock prior to spray drying. For the purposes of the present invention this feed stock will also preferably comprise one or more bioactive agents, one or more surfactants, or one or more excipients. Of course, combinations of the aforementioned components are also within the scope of the invention.

While not limiting the invention in any way, it is hypothesized that, as the aqueous feed component evaporates during spray drying it leaves a thin crust at the surface of the particle. The resulting particle wall or crust, formed during the initial moments of spray drying, appears to trap any high boiling blowing agents as hundreds of emulsion droplets (ca. 200–300 nm). As the drying process continues, the pressure inside the particulate increases, thereby vaporizing at least part of the incorporated blowing agent and, forcing it through the relatively thin crust. This venting or outgassing, apparently leads to the formation of pores or other defects in the crust. At the same time, remaining particulate components (possibly including some blowing agent) migrate from the interior to the surface as the particle solidifies. This migration apparently slows during the drying process as a result of increased resistance to mass transfer caused by an increased internal viscosity. Once the migration ceases, the particle solidifies, leaving vesicles, vacuoles or voids where the emulsifying agent resided. The number of pores, their size, and the resulting wall thickness is largely dependent on the nature of the selected blowing agent (i.e. boiling point), its concentration in the emulsion, total solids concentration, and the spray-drying conditions.

It has been surprisingly found that substantial amounts of these relatively high boiling point blowing agents may be retained in the resulting spray dried product. That is, the spray dried perforated microstructures may comprise as much as 5%, 10%, 20%, 30% or even 40% w/w of the blowing agent. In such cases, higher production yields were obtained as a result an increased particle density caused by residual blowing agent. It will be appreciated by those skilled in the art that, this retained fluorinated blowing agent may alter the surface characteristics of the perforated microstructures and further increase the stability of the respiratory dispersions. 25 Conversely, the residual blowing agent can easily be removed with a post-production evaporation step in a vacuum oven. Optionally, pores may be formed by spray drying a bioactive agent and an excipient that can be removed from the formed microspheres under a vacuum.

In any event, typical concentrations of blowing agent in the feed stock are between 5% and 100% w/v, and more preferably, between about 20% to 90% w/v. In other embodiments, blowing agent concentrations will preferably be greater than about 10%, 20%, 30%, 40% 50% or even 60% w/v. Yet other feed stock emulsions may comprise 70%, 80%, 90% or even 95% w/v of the selected high boiling point compound.

In preferred embodiments, another method of identifying the concentration of blowing agent used in the feed is, to provide it as a ratio of the concentration of the blowing agent to that of the stabilizing surfactant (i.e. phospholipid) in the precursor emulsion. For fluorocarbon blowing agents such as perfluorooctyl bromide and phosphatidyicholine, the ratio may be termed a perfluorocarbon/phosphatidylcholine ratio (or PFC/PC ratio). Of course, it will be appreciated that other compatible surfactants may also be used to provide compatible particulates. In any event, the PFCIPC ratio will typically range from about 1 to about 60 and more preferably, from about 10 to about 50. For preferred embodiments the ratio will generally be greater than about 5, 10, 20, 25, 30, 40 or even 50. In this respect, FIG. 1 shows a series of pictures taken of perforated microstructures formed of phosphatidylcholine (PC) using various amounts of perfluorooctyl bromide (PFC), a relatively high boiling point fluorocarbon as the blowing agent. The PFCJPC ratios are provided under each subset of pictures, i.e. from 1A to 1F. Formation and imaging conditions are discussed in greater detail in Examples I and II below. With regard to the micrographs, the column on the left shows the intact microstructures while the column on the right illustrates cross-sections of fractured microstructures from the same preparations.

As may easily be seen in the FIG. 1, the use of higher PFC/PC ratios provides structures of a more hollow and porous nature. More particularly, those methods employing a PFC/PC ratio of greater than about 4.8 tended to provide structures that are particularly compatible with the dispersions disclosed herein. Similarly, FIG. 2, a micrograph which will be discussed in more detail in Example II below, illustrates a preferably porous morphology obtained by using higher boiling point blowing agents (in this case perfluorodecalin).

While relatively high boiling point blowing agents comprise one preferred aspect of the instant invention, it will be appreciated that more conventional blowing or inflating agents may also be used to provide compatible perforated microstructures. Generally, the inflating agent can be any material that will turn to a gas at some point during the spray drying or post-production process. Suitable agents include:

1. Dissolved low-boiling (below 100° C.) solvents with limited miscibility with aqueous solutions, such as methylene chloride, acetone and carbon disulfide used to saturate the solution at room temperature.
2. A gas, e.g. $CO_2$ or $N_2$, used to saturate the solution at room temperature and elevated pressure (e.g. 3 bar). The droplets are then supersaturated with the gas at 1 atmosphere and 100° C.
3. Emulsions of immiscible low-boiling (below 100° C.) liquids such as Freon 113, perfluoropentane, perfluorohexane, perfluorobutane, pentane, butane, FC-11, FC-11B , FC-11B2, FC-12B2, FC-21, FC-21B1, FC-21B2, FC-31B1, FC-113A, FC-122, FC-123, FC-132, FC-133, FC-141, FC-141B, FC-142, FC-151, FC-152, FC-1112, FC-1121 and FC-1131.

With respect to these lower boiling point inflating agents, they are typically added to the feed stock in quantities of about 1% to 40% v/v of the surfactant solution. Approximately 15% v/v inflating agent has been found to produce a spray dried powder that may be used to form the stabilized dispersions of the present invention.

Regardless of which blowing agent is ultimately selected, it has been found that compatible perforated microstructures or particles may be produced particularly efficiently using a Büilchi mini spray drier (model B-191, Switzerland). As will be appreciated by those skilled in the art, the inlet temperature and the outlet temperature of the spray drier are not critical but will be of such a level to provide the desired particle size and to result in a product that has the desired activity of the medicament. In this regard, the inlet and outlet temperatures are adjusted depending on the melting characteristics of the formulation components and the composition of the feed stock. The inlet temperature may thus be between 60° C. and 170° C., with the outlet temperatures of about 40° C. to 120° C. depending on the composition of the feed and the desired particulate characteristics. Preferably, these temperatures will be from 90° C. to 120° C. for the inlet and from 60° C. to 90° C. for the outlet. The flow rate which is used in the spray drying equipment will generally be about 3 ml per minute to about 5 ml per minute. The atomizer air flow rate may vary between values of 1,200 liters per hour to about 3,900 liters per hour. Commercially available spray dryers are well known to those in the art, and suitable settings for any particular dispersion can be readily determined through standard empirical testing, with due reference to the examples that follow. Of course, the conditions may be adjusted so as to preserve biological activity in larger molecules such as proteins or peptides.

Particularly preferred embodiments of the present invention comprise spray drying preparations comprising a surfactant such as a phospholipid and at least one bioactive agent. In other embodiments, the spray drying preparation may further comprise an excipient comprising a hydrophilic moiety such as, for example, a carbohydrate (i.e. glucose, lactose, or starch) in addition to any selected surfactant. In this regard, various starches and derivatized starches are suitable for use in the present invention. Other optional components may include conventional viscosity modifiers, buffers such as phosphate buffers or, other conventional biocompatible buffers or pH adjusting agents such as acids or bases, and osmotic agents (to provide isotonicity, hyperosmolarity, or hyposmolarity). Examples of suitable salts include sodium phosphate (both monobasic and dibasic), sodium chloride, calcium phosphate, calcium chloride and other physiologically acceptable salts.

Whatever components are selected, the first step in particulate production, typically comprises feed stock preparation. Preferably, the selected drug is dissolved in water to produce a concentrated solution. The drug may also be dispersed directly in the emulsion, particularly in the case of water insoluble agents. Alternatively, the drug may be incorporated in the form of a solid particulate dispersion. The concentration of the drug used is dependent on the dose of drug required in the final powder and the performance or efficiency of the nebulization device. As needed, co-surfactants such as poloxamer 188 or span 80 may be added to this annex solution. Additionally, excipients such as sugars and starches can also be added.

In selected embodiments, an oil-in-water emulsion is then formed in a separate vessel. The oil employed is preferably a fluorocarbon (e.g., perfluorooctyl bromide, perfluorodecalin), which is emulsified using a surfactant such as a long chain saturated phospholipid. For example, one gram of phospholipid may be homogenized in 150 g hot distilled water (e.g., 60° C.) using a suitable high shear mechanical mixer (e.g., Ultra-Turrax model T-25 mixer) at 8000 rpm for 2 to 5 minutes. Typically, 5 to 25 g of fluorocarbon is added dropwise to the dispersed surfactant solution while mixing. The resulting perfluorocarbon-in-water emulsion is then processed using a high pressure homogenizer to reduce the particle size. Typically, the emulsion is processed at 12,000 to 18,000 psi, 5 discrete passes and kept at 50 to 80° C.

The drug solution and perfluorocarbon emulsion are then combined and fed into the spray dryer. Typically, the two preparations will be miscible as the emulsion will preferably comprise an aqueous continuous phase. While the bioactive agent is solubilized separately for the purposes of the instant discussion, it will be appreciated that, in other embodiments, the bioactive agent may be solubilized (or dispersed) directly in the emulsion. In such cases, the bioactive emulsion is simply spray dried without combining a separate drug preparation.

In any event, operating conditions such as inlet and outlet temperature, feed rate, atomization pressure, flow rate of the drying air, and nozzle configuration can be adjusted in accordance with the manufacturer's guidelines in order to produce the required particle size and production yield of the resulting dry microstructures. Exemplary settings are as follows: an air inlet temperature between 60° C. and 170° C.; an air outlet between 40° C. to 120° C.; a feed rate between 3 ml to about 15 ml per minute; and an aspiration setting of 300 L/min and an atomization air flow rate between 1,200 to 2,800.L/hr. The selection of appropriate apparatus and processing conditions are well within the purview of a skilled artisan in view of the teachings herein, and may be accomplished without undue experimentation. In any event, the use of these and substantially equivalent methods provide for the formation of hollow, porous, aerodynamically light microspheres, with particle diameters appropriate for aerosol deposition into the lung. As described above, such particles are particularly effective in the formation of stabilized dispersions that are extremely compatible with the inhalation systems and nebulization techniques described more fully below.

Along with spray drying, particulates or perforated microstructures useful in the present invention may be formed by lyophilization. Those skilled in the art will appreciate that lyophilization is a freeze-drying process in which water is sublimed from the composition after it is frozen. The particular advantage associated with the lyophilization process is that, biologicals and pharmaceuticals that are relatively unstable in an aqueous solution can be dried without elevated temperatures (thereby eliminating the adverse thermal effects), and then stored in a dry state where there are few stability problems. With respect to the instant invention, such techniques are particularly compatible with the incorporation of peptides, proteins, genetic material and other natural and synthetic macromolecules in particulates or perforated microstructures without compromising physiological activity. Methods for providing lyophilized particulates are known to those of skill in the art and, it would clearly not require undue experimentation to provide dispersion compatible microstructures in accordance with the teachings herein. Accordingly, to the extent that lyophilization processes may be used to provide microstructures having the desired porosity and size, they are in conformance with the teachings herein and are expressly contemplated as being within the scope of the instant invention.

In addition to the aforementioned techniques, perforated microstructures or particles of the present invention may also be formed using a double emulsion method. In the double emulsion method, the medicament is first dispersed in a polymer dissolved in an organic solvent (e.g. methylene chloride) by sonication or homogenization. This primary emulsion is then stabilized by forming a multiple emulsion in a continuous aqueous phase containing an emulsifier such as polyvinylalcohol. The organic solvent is then removed by evaporation or extraction using conventional techniques and apparatus. The resulting microspheres are washed, filtered and lyophilized prior to dispersion into suspension medium in accordance with the present invention.

While particulate suspensions comprising a non-liquid dispersed phase are particularly compatible with the present invention, it will be appreciated that, as discussed above, the stabilized dispersions may also comprise liquid-in-liquid colloidal systems, e.g. reverse emulsions and microemulsions. Those skilled in the art will appreciate that such systems are known in the art and stabilized dispersions compatible with the teachings herein may be provided without undue experimentation. In this regard, any reverse emulsion or microemulsion that is capable of being nebulized to provide a therapeutically effective aerosol for pulmonary administration is contemplated as being within the scope of the present invention. Preferably, the emulsions will be water-in-fluorochemical emulsions. That is, the selected reverse emulsion or microemulsion will preferably comprise a fluorochemical disperse phase with the other phase being aqueous in nature. Exemplary reverse emulsions useful with the present invention are disclosed in U.S. Pat. No. 5,770,585, pending U.S. Ser. No. 08/487,612 and pending U.S. Ser. No. 08/478,824 with each of the foregoing references incorporated herein by reference. Such preparations may be stabilized by fluorinated or non-fluorinated surfactants. With respect to this aspect of the invention, many of the fluorochemicals useful in the disclosed liquid-iii-liquid preparations are the same as those that are useful as suspension mediums in the disclosed particulate dispersions. Accordingly, while the following discussion is primarily directed to compatible suspension mediums for the distribution of non-liquid particles, it will be appreciated that the same compounds (e.g. fluorochemicals) are useful in liquid-in-liquid dispersions that are compatible with the instant invention. Thus, while the term "suspension medium" or media will be used below, it should be understood that, these same compounds may comprise emulsion phases in accordance with the teachings herein.

Regardless of the selected colloidal system, it is an advantage of the present invention that biocompatible non-aqueous compounds may be used as suspension mediums or as a continuous phase. Particularly preferred suspension media are compatible with use in nebulizers. That is, they will be able to form aerosols upon the application of energy thereto. In general, the selected suspension medium should be biocompatible (i.e. relatively non-toxic) and non-reactive with respect to the suspended perforated microstructures comprising the bioactive agent. Preferred embodiments comprise suspension media selected from the group consisting of fluorochemicals, fluorocarbons (including those substituted with other halogens), perfluorocarbons, fluorocarbon/hydrocarbon diblocks, hydrocarbons, alcohols, ethers, or combinations thereof. It will be appreciated that, the suspension medium may comprise a mixture of various compounds selected to impart specific characteristics. It will also be appreciated that the perforated microstructures are preferably insoluble in the suspension medium, thereby providing for stabilized medicament particles, and effectively protecting a selected bioactive agent from degradation, as might occur during prolonged storage in an aqueous solution. In preferred embodiments, the selected suspension medium is bacteriostatic. The suspension formulation also protects the bioactive agent from degradation during the nebulization process.

As indicated above the suspension media may comprise any one of a number of different compounds including hydrocarbons, fluorocarbons or hydrocarbon/fluorocarbon diblocks. In general, the contemplated hydrocarbons or highly fluorinated or perfluorinated compounds may be linear, branched or cyclic, saturated or unsaturated compounds. Conventional structural derivatives of these fluorochemicals and hydrocarbons are also contemplated as being within the scope of the present invention as well. Selected embodiments comprising these totally or partially fluorinated compounds may contain one or more hetero-atoms and/or atoms of bromine or chlorine. Preferably, these fluorochemicals comprise from 1 to 16 carbon atoms and include, but are not limited to, linear, cyclic or polycyclic perfluoroalkanes, bis(perfluoroalkyl)alkenes, perfluoroethers, perfluoroamines, perfluoroalkyl bromides and perfluoroalkyl chlorides such as dichlorooctane. Particularly preferred fluorinated compounds for use in the suspension medium may comprise perfluorooctyl bromide $C_8F_{17}Br$ (PFOB or perflubron), dichlorofluorooctane $C_8F_{16}Cl_2$. and the hydrofluoroalkane perfluorooctyl ethane $C_8F_{17}C_2H_5$ (PFOE). With respect to other embodiments, the use of perfluorohexane or perfluoropentane as the suspension medium is especially preferred.

More generally, exemplary fluorochemicals which are contemplated for use in the present invention generally include halogenated fluorochemicals (i.e. $C_nF_{2n+}X$, $XC_nF_{2n}X$, where n=2–10, X=Br, Cl or I) and, in particular, 1-bromo-F-butane n-$C_4F_9Br$, $_1$-bromo-F-hexane (n-$C_6F_{13}Br$), 1-bromo-F-heptane (n-$C_7F_{15}Br$), 1,4-dibromo-F-butane and 1,6-dibromo-F-hexane. Other useful brominated fluorochemicals are disclosed in U.S. Pat. No. 3,975,512 to Long and are incorporated herein by reference. Specific fluorochemicals having chloride substituents, such as perfluorooctyl chloride (n-$C_8F_{17}Cl$), 1,8-dichloro-F-octane (n-$ClC_8F_{16}Cl$), 1,6-dichloro-F-hexane (n-$ClC_6F_{12}Cl$), and 1,4-dichloro-F-butane (n-$ClC_4F_8Cl$) are also preferred.

Fluorocarbons, fluorocarbon-hydrocarbon compounds and halogenated fluorochemicals containing other linkage groups, such as esters, thioethers and amines are also suitable for use as suspension media in the present invention. For instance, compounds having the general formula, $C_nF_{2n+1}OC_mF_{2m+1}$, or $C_nF_{2n+1}CH=CHC_mF_{2m+1}$, (as for example $C_4F_9CH=CHC_4F_9$ (F-44E), i-$C_3F_9CH=CHC_6F_{13}$ (F-i36E), and $C_6F_{13}CH=CHC_6F_{13}$ (F-66E)) where n and different and n and m are integers from about 2 to about 12 are compatible with teachings herein. Useful fluorochemical-hydrocarbon diblock and triblock compounds include those with the general formulas $C_nF_{2n+1}$—$C_mH_{2m+1}$ and $C_nF_{2n+1}C_mH_{2m-1}$, where n=2–12; m=2–16 or $C_pH_{2p+1}$—$C_nF_{2n}$—$C_mH_{2m+1}$, where p=1–12, m=1–12 and n=2–12. Preferred compounds of this type include $C_8F_{17}C_2H5$, $C_6F_{13}C_{10}H_{21}$, $C_8F_{17}C_8H_{17}$, $C_6F_{13}CH=CHC_6H_{13}$ and $C_8F_{17}CH=CHC_{10}H_{21}$. Substituted ethers or polyethers (i.e. $XC_nF_{2n}OC_mF_{2m}X$, $XCFOC_nF_{2n}OCF_2X$, where n and m=1–4, X=Br, Cl or I) and fluorochemical-hydrocarbon ether diblocks or triblocks (i.e. $C_nF_{2n+1}$—O—$C_mH_{2m+1}$, where n=2–10; m=2–16 or $C_pH_{2p+1}$ —O—$C_nF_{2n}$—O—$C_mH_{2m+1}$, where p=2–12, m=1–12 and n=2–12) may also used as well as $C_nF_{2n+1}O$—$C_mF_{2m}OC_pH_{2p+1}$, wherein n, m and p are from 1–12. Furthermore, depending on the application, perfluoroalkylated ethers or polyethers may be compatible with the claimed dispersions.

Polycyclic and cyclic fluorochemicals, such as $C_{10}F_{18}$ (F-decalin or perfluorodecalin), perfluoroperhydrophenanthrene, perfluorotetramethylcyclohexane (AP-144) and perfluoro n-butyldecalin are also within the scope of the invention. Additional useful fluorochemicals include perfluorinated amines, such as F-tripropylamine ("FTPA") and F-tributylamine ("FTBA"). F-4-methyloctahydroquinolizine ("FMOQ"), F-N-methyl-decahydroisoquinoline ("FMIQ"), F-N-methyldecahydroquinoline ("FHQ"), F-N-cyclohexylpyrrolidine ("FCHP") and F-2-butyltetrahydrofuran ("FC-75" or "FC-77"). Still other useful fluorinated compounds include perfluorophenanthrene, perfluoromethyldecalin, perfluorodimethylethylcyclohexane, perfluorodimethyldecalin, perfluorodiethyldecalin, perfluoromethyladamantane, perfluorodimethyladamantane. Other contemplated fluorochemicals having nonfluorine substituents, such as, perfluorooctyl hydride, and similar compounds having different numbers of carbon atoms are also useful. Those skilled in the art will further appreciate that other variously modified fluorochemicals are encompassed within the broad definition of fluorochemical as used in the instant application and suitable for use in the present invention. As such, each of the foregoing compounds may be used, alone or in combination with other compounds to form the stabilized dispersions of the present invention.

Specific fluorocarbons, or classes of fluorinated compounds, that may be useful as suspension media include, but are not limited to, fluoroheptane, fluorocycloheptane fluoromethylcycloheptane, fluorohexane, fluorocyclohexane, fluoropentane, fluorocyclopentane, fluoromethylcyclopentane, fluorodimethylcyclopentanes, fluoromethylcyclobutane, fluorodimethylcyclobutane, fluorotrimethylcyclobutane, fluorobutane, fluorocyclobutane, fluoropropane, fluoroethers, fluoropolyethers and fluorotriethylamines. Such compounds are generally environmentally sound and are biologically non-reactive.

While any fluid compound capable of producing an aerosol upon the application of energy may be used in conjunction with the. present invention, the selected suspension medium will preferably have a vapor pressure less than about 5 atmospheres and more preferably less than about 2 atmospheres. Unless otherwise specified, all vapor pressures recited herein are measured at 25° C. In other embodiments, preferred suspension media compounds will have vapor pressures on the order of about 5 torr to about 760 torr, with more preferable compounds having vapor pressures on the order of from about 8 torr to about 600 torr, while still more preferable compounds will have vapor pressures on the order of from about 10 torr to about 350 torr. Such suspension media may be used in conjunction with compressed air nebulizers, ultrasonic nebulizers or with mechanical atomizers to provide effective ventilation therapy. Moreover, more volatile compounds may be mixed with lower vapor pressure components to provide suspension media having specified physical characteristics selected to further improve stability or enhance the bioavailability of the dispersed bioactive agent.

Other embodiments of the present invention will comprise suspension media that boil at selected temperatures under ambient conditions (i.e. 1 atm). For example, preferred embodiments will comprise suspension media compounds that boil above 0° C., above 5° C., above 10° C., above 15°, or above 20° C. In other embodiments, the suspension media compound may boil at or above 25° C. or at or above 30° C.

In yet other embodiments, the selected suspension media compound may boil at or above human body temperature (i.e. 37° C.), above 45° C., 55° C., 65° C., 75° C, 85° C. or above 100° C.

It will further be appreciated that one of ordinary skill in the art can readily determine other compounds that would perform suitably in the present invention which apparently do not exhibit a desirable vapor pressure and/or viscosity. Rather, it will be understood that, certain compounds outside the preferred ranges of vapor pressure or viscosity can be used if they provide the desired aerosolized medicament.

The stabilized suspensions or dispersions of the present invention may be prepared by dispersal of the microstructures in the selected suspension medium which may then be placed in a container or reservoir. In this regard, the stabilized preparations of the present invention can be made by simply combining the components in sufficient quantity to produce the final desired dispersion concentration. Although the microstructures readily disperse without mechanical energy, the application of mechanical energy to aid in dispersion (e.g. with the aid of sonication) is contemplated, particularly for the formation of stable emulsions or reverse emulsions. Alternatively, the components may be mixed by simple shaking or other type of agitation. The process is preferably carried out under anhydrous conditions to obviate any adverse effects of moisture on suspension stability. Once formed, the dispersion has a reduced susceptibility to flocculation and sedimentation.

It will also be understood that, other components can be included in the pharmaceutical compositions of the present invention. For example, osmotic agents, stabilizers, chelators, buffers, viscosity modulators, salts, and sugars can be added to fine tune the stabilized dispersions for maximum life and ease of administration. Such components may be added directly to the suspension medium, ether phase of an emulsion or associated with, or incorporated in, dispersed particles or perforated microstructures. Considerations such as sterility, isotonicity, and biocompatibility may govern the use of conventional additives to the disclosed compositions. The use of such agents will be understood to those of ordinary skill in the art and, the specific quantities, ratios, and types of agents can be determined empirically without undue experimentation.

Administration of bioactive agent may be indicated for the treatment of mild, moderate or severe, acute or chronic symptoms or for prophylactic treatment. Moreover, the bioactive agent may be administered to treat local or systemic conditions or disorders. It will be appreciated that, the precise dose administered will depend on the age and condition of the patient, the particular medicament used and the frequency of administration, and will ultimately be at the discretion of the attendant physician. When combinations of bioactive agents are employed, the dose of each component of the combination will generally be that employed for each component when used alone.

As discussed throughout the specification, the stabilized dispersions disclosed herein, are preferably administered to the lung or pulmonary air passages of a patient via aerosolization, such as with a nebulizer. Nebulizers are well known in the art and could easily be employed for administration of the claimed dispersions without undue experimentation. Breath activated nebulizers, as well as those comprising other types of improvements which have been, or will be, developed are also compatible with the stabilized dispersions and present invention and are contemplated as being with in the scope thereof.

While compatible bioactive agents may be administered using various systems, it will be appreciated that, in particularly preferred embodiments, the stabilized dispersions disclosed herein will be administered to the lung or pulmonary air passages of a patient via nebulization. Nebulizers are well known in the art and could easily be employed for administration of the claimed dispersions without undue experimentation.

Nebulizers work by forming aerosols, that is converting a bulk liquid into small droplets suspended in a breathable gas. Here, the aerosolized medicament to be administered (preferably to the pulmonary air passages) will comprise small droplets of suspension medium associated with relatively non-porous particles, perforated microstructures, or disperse liquid phase comprising a bioactive agent. In such embodiments, the stabilized dispersions of the present invention will typically be placed in a fluid reservoir operably associated with a nebulizer. The specific volumes of preparation provided, means of filling the reservoir, etc., will largely be dependent on the selection of the individual nebulizer and is well within the purview of the skilled artisan. Of course, the present invention is entirely compatible with single-dose nebulizers and multiple dose nebulizers.

In any event, nebulizer mediated aerosolization typically requires an input of energy in order to produce the increased surface area of the droplets and, in some cases, to provide transportation of the atomized or aerosolized medicament. One common mode of aerosolization is forcing a stream of fluid to be ejected from a nozzle, whereby droplets are formed. With respect to nebulized administration, additional energy is usually imparted to provide droplets that will be sufficiently small to be transported deep into the lungs. Thus, additional energy is needed, such as that provided by a high velocity gas stream or a piezoelectric crystal. Two popular types of nebulizers, jet nebulizers and ultrasonic nebulizers, rely on the aforementioned methods of applying additional energy to the fluid during atomization.

The jet nebulizer is well known and in widespread use. In a jet nebulizer, compressed air is forced into a device containing a liquid to be aerosolized, such as one of the suspensions of the present invention. The compressed air draws the liquid through one or more small openings, thus generating the aerosol. The high velocity of the compressed air provides sufficient energy to enable the formation of droplets small enough for inhalation. To aid in formation of uniformly smaller droplets, the droplets initially impact a baffle. There may be other impaction sites onto which the droplets may be directed before the aerosol is carried out of the nebulizer by the flow of the compressed air. In preferred embodiments the compressed air may be saturated with the suspension medium. This would allow the aerosolized droplets to be deposited in the lung, possibly facilitating enhanced spreading of bioactive agent after initial deposition.

Ultrasonic nebulizers do not require the use of compressed air, and thus, may be similar to MDIs as to compactness and portability, though they operate under different physical principles. Preferred ultrasonic nebulizers are those which are fairly small, portable, battery-powered and capable of delivering several doses, each of which comprises a single bolus of aerosolized solution. Such nebulizers may be termed single-bolus nebulizers. Most devices are manually actuated, but some devices exist which are breath actuated. Breath actuated devices work by releasing aerosol when the device senses the patient inhaling through a circuit. Breath actuated nebulizers may also be placed in-line on a ventilator circuit to release aerosol into the air flow which comprises the inspiration gases for a patient.

The heart of most species of ultrasonic nebulizer is a transducer made from a piezoelectric crystal. When oscillating energy is applied to the piezoelectric crystal, it will vibrate at the same frequency as the applied energy which is preferably in the ultrasonic range. This motion, when transmitted into a liquid, provides the energy needed to aerosolize the liquid. The droplet size (count median diameter) formed by this method is a function of the excitation frequency, the density of the liquid, and the surface tension of the liquid, whereas the rate of atomization is a function of the viscosity, surface tension, and vapor pressure.

One type of nebulizer is the Respimat (Boehringer Ingelheim, Germany) which is manually actuated, hand-held and battery operated. When the patient squeezes a trigger on the device, a droplet of solution (about 100 µl) is metered into a piezoelectric plate about 1 cm in diameter. When energy is applied, the plate vibrates at about 10 MHz, resulting in the aerosolization of the solution which may then be inhaled by a patient.

Another type of ultrasonic nebulizer is the AeroDose™ (AeroGen, Sunnyvale, Calif.). (DeYoung, "The AeroDose Multidose Inhaler Device Design and Delivery Characteristics," Respiratory Drug Delivery VI, 1998, p. 91) The battery-powered AeroDose operates by means of a plate containing several hundred holes which vibrates at ultrasonic frequencies. When the top of the device is pressed down, a metering pump delivers a dose of liquid from a multidose canister to the plate. The device is breath actuated, with aerosolization beginning when the device senses the inspiration of the patient. The investigators for the AeroDose report that they are able to achieve a median mass aerodynamic diameter of 1.9 to 2.0 µm using this device.

Yet another type of ultrasonic nebulizer is that in PCT Publication No. WO92/11050 to Robertson, et. al., In the Robertson device, the solution or other material to be nebulized is drawn through numerous tiny holes in a metal plate which vibrates through the use of a piezoelectric device. When energy is applied, the aerosol is formed and will continue to form as long as energy is delivered to the piezoelectric crystal. Thus, depending on the amount of time that the device is left on, it may serve as either a single bolus device or a continuous nebulizer.

As seen above, ultrasonic nebulization devices may act by ultrasonic energy alone, or may use ultrasonic energy in combination with other methods of aerosolization such as forcing or drawing a liquid or suspension through a material with very small openings. Yet, regardless of the type of nebulizer selected, the stabilized dispersions of the present invention provide a significant advantage due to their relatively homogeneous dispersion of the incorporated bioactive agent over a period of time. That is, the homogeneous dispersion of the incorporated particulates ensures that the amount of bioactive agent administered will be consistent no matter which fraction of the preparation in the fluid reservoir is actually nebulized in each individual actuation of the nebulizer. Similarly, when used for continuous administration over an extended period the stable, homogeneous dispersions of the present invention ensure that relatively constant levels of bioactive agent are delivered during each incremental period of time.

In any event, it should be noted that the preceding examples of nebulizers are only for exemplary purposes. As will be recognized by one skilled in the art, other types of nebulizers, whether currently known or later invented, may also be used for administration of the stabilized dispersions of the present invention.

It will be appreciated that, the stabilized preparations for use in nebulizers of the present invention may be advantageously supplied to the physician or other health care professional, in a sterile, prepackaged or kit form. More particularly, the formulations may be supplied as stable, preformed dispersions ready for administration or, as separate ready to mix components. When provided in a ready to use form, the dispersions may be packaged in single use containers or reservoirs, as well as in multi-use containers or reservoirs. In either case, the container or reservoir may be associated with the selected nebulizer and used as described herein. When provided as individual components (e.g., as powdered microspheres and as neat suspension medium) the stabilized preparations may then be formed at any time prior to use by simply combining the contents of the containers as directed. Additionally, such kits may contain a number of ready to mix, or prepackaged components that may be packaged individually so that the user can then select the desired component(s) for the particular indication or. use. In this regard, the user may then substitute selected components at will, or as indicated, during a particular course of treatment. It will also be appreciated that such kits may optionally include a nebulizer or that the preparation may be supplied in a disposable nebulizer.

The foregoing description will be more fully understood with reference to the following Examples. Such Examples, are, however, merely representative of preferred methods of practicing the present invention and should not be read as limiting the scope of the invention.

I Preparation of Hollow Porous Particles of Gentamicin Sulfate by Spray-Drying 40 to 60 ml of the following solutions were prepared for spray drying:

50% w/w hydrogenated phosphatidylcholine, E-100-3 (Lipoid K G, Ludwigshafen, Germany)
50% w/w gentamicin sulfate (Amresco, Solon, Ohio.)
Perfluorooctylbromide, Perflubron (NMK, Japan)
Deionized water Perforated microstructures comprising gentamicin sulfate were prepared by a spray drying technique using a B-191 Mini Spray-Drier (Büchi, Flawil, Switzerland) under the following conditions: aspiration: 100%, inlet temperature: 85° C.; outlet temperature: 61° C.; feed pump: 10%; $N_2$ flow: 2,800 L/hr. Variations in powder porosity were examined as a function of the blowing agent concentration.

Fluorocarbon-in-water emulsions of perfluorooctyl bromide containing a 1:1 w/w ratio of phosphatidylcholine (PC), and gentamicin sulfate were prepared varying only the PFC/PC ratio. 1.3 grams of hydrogenated egg phosphatidylcholine was dispersed in 25 mL deionized water using an Ultra-Turrax mixer (model T-25) at 8000 rpm for 2 to 5 minutes (T=60–70° C.). A range from 0 to 40 grams of perflubron was added dropwise during mixing (T=60–70° C.). After addition was complete, the fluorocarbon-in-water emulsion was mixed for an additional period of not less than 4 minutes. The resulting coarse emulsions were then homogenized under high pressure with an Avestin (Ottawa, Canada) homogenizer at 15,000 psi for 5 passes. Gentamicin sulfate was dissolved in approximately 4 to 5 mL deionized water and subsequently mixed with the perflubron emulsion immediately prior to the spray dry process. The gentamicin powders were then obtained by spray drying using the conditions described above. A free flowing pale yellow powder was obtained for all perflubron containing formulations. The yield for each of the various formulations ranged from 35% to 60%.

II Morphology of Gentamicin Sulfate Spray-Dried Powders

A strong dependence of the powder morphology, degree of porosity, and production yield was observed as a function of the PFC/PC ratio by scanning electron microscopy (SEM). A series of six SEM micrographs illustrating these observations, labeled 1A1 to 1F1, are shown in the left hand column of FIG. 1. As seen in these micrographs, the porosity and surface roughness was found to be highly dependent on the concentration of the blowing agent, where the surface roughness, number and size of the pores increased with increasing PFC/PC ratios. For example, the formulation devoid of perfluorooctyl bromide produced microstructures that appeared to be highly agglomerated and readily adhered to the surface of the glass vial. Similarly, smooth, spherically shaped microparticles were obtained when relatively little (PFC/PC ratio=1.1 or 2.2) blowing agent was used. As the PFC/PC ratio was increased the porosity and surface roughness increased dramatically.

As shown in the right hand column of FIG. 1, the hollow nature of the microstructures was also enhanced by the incorporation of additional blowing agent. More particularly, the series of six micrographs labeled 1A2 to 1F2 show cross sections of fractured microstructures as revealed by transmission electron microscopy (TEM). Each of these images was produced using the same microstructure preparation as was used to produce the corresponding SEM micrograph in the left hand column. Both the hollow nature and wall thickness of the resulting perforated microstructures appeared to be largely dependent on the concentration of the selected blowing agent. That is, the hollow nature of the preparation appeared to increase and the thickness of the particle walls appeared to decrease as the PFC/PC ratio increased. As may be seen in FIGS. 1A2 to 1C2 substantially solid structures were obtained from formulations containing. little or no fluorocarbon blowing agent. Conversely, the perforated microstructures produced using a relatively high PFC/PC ratio of approximately 45 (shown in FIG. 1F2 proved to be extremely hollow with a relatively thin wall ranging from about 43.5 to 261 nm. Both types of particles are compatible for use in the present invention.

III Preparation of Hollow Porous Particles of Albuterol Sulfate by Spray-Drying Hollow porous albuterol sulfate particles were prepared by a spray-drying technique with a B-191 Mini Spray-Drier (Büchi, Flawil, Switzerland) under the following spray conditions: aspiration: 100%, inlet temperature: 85° C.; outlet temperature: 61° C.; feed pump: 10%; $N_2$ flow 2,800 L/hr. The feed solution was prepared by mixing two solutions A and B immediately prior to spray drying.

Solution A: 20 g of water was used to dissolve 1 g of albuterol sulfate (Accurate Chemical, Westbury, N.Y.) and 0.021 g of poloxamer 188 NF grade (BASF, Mount Olive, N.J.). Solution B: A fluorocarbon-in-water emulsion stabilized by phospholipid was prepared in the following manner. The phospholipid, 1 g EPC-100-3 (Lipoid K G, Ludwigshafen, Germany), was homogenized in 150 g of hot deionized water (T=50 to 60° C.) using an Ultra-Turrax mixer (model T-25) at 8000 rpm for 2 to 5 minutes (T=60–70° C.). 25 g of perfluorooctyl bromide (Atochem, Paris, France) was added dropwise during mixing. After the fluorocarbon was added, the emulsion was mixed for a period of not less than 4 minutes. The resulting coarse emulsion was then passed through a high pressure homogenizer (Avestin, Ottawa, Canada) at 18,000 psi for 5 passes.

Solutions A and B were combined and fed into the spray-dryer under the conditions described above. A free flowing white powder was collected at the cyclone separator. The hollow porous albuterol sulfate particles had a volume-weighted mean aerodynamic diameter of 1.18±1.42 μm as determined by a time-of-flight analytical method (Aerosizer, Amherst Process Instruments, Amherst, Mass.). Scanning electron microscopy (SEM) analysis showed the powders to be spherical and highly porous. The tap density of the powder was determined to be less than 0.1 g/cm$^3$.

This foregoing example serves to illustrate the inherent diversity of the present invention as a drug delivery platform capable of effectively incorporating any one of a number of pharmaceutical agents. The principle is further illustrated in the next example.

IV Formation of Porous Particulate Microstructures Comprising Mixtures of Long-Chain/Short-Chain Phospholipids and Albuterol Sulfate A dispersion for spray-drying was prepared as described above, with the difference that 1 g of DSPC was .dispersed with 100 mg of a short-chain phospholipid, dioctylphosphatidylcholine (DOPC) (Avanti Polar Lipids, Alabaster, Ala.). The composition of the spray feed is shown in Table II immediately below. The resulting yield was 50%.

TABLE II

Composition of the Spray Feed

| Component | Quantity |
|---|---|
| Disteroylphosphatidylcholine (DSPC) | 1 g |
| Dioctanoylphosphatidylcholine (DOPC) | 0.1 g |
| Albuterol Sulfate | 1 g |
| Perfluorohexane | 1 g |
| Water | 60 g |

V Preparation of Hollow Porous Particles of Cromolyn Sodium by Spray-Drying

Perforated microstructures comprising cromolyn sodium were prepared by a spray-drying technique with a B-191 Mini Spray-Drier (Büchi, Flawil, Switzerland) under the following spray conditions: aspiration: 100%, inlet temperature: 85° C.; outlet temperature: 61° C.; feed pump: 10%; $N_2$ flow: 2,800 L/hr. The feed solution was prepared by mixing two solutions A and B immediately prior to spray drying.

Solution A: 20 g of water was used to dissolve 1 g of cromolyn sodium (Sigma Chemical Co, St. Louis, Mo.) and 0.021 g of poloxamer 188 NF grade (BASF, Mount Olive, N.J.).

Solution B: A fluorocarbon-in-water emulsion stabilized by phospholipid was prepared in the following manner. The phospholipid, 1 g EPC-100-3 (Lipoid K G, Ludwigshafen, Germany), was homogenized in 150 g of hot deionized water (T=50 to 60° C.) using an Ultra-Turrax mixer (model T-25) at 8000 rpm for 2 to 5 minutes (T=60–70° C.). 27 g of perfluorodecalin (Air Products, Allentown, Pa.) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes.

Solutions A and B were combined and fed into the spray dryer under the conditions described above. A free flowing pale yellow powder was collected at the cyclone separator. The hollow porous cromolyn sodium particles had a volume-weighted mean aerodynamic diameter of 1.23±1.31 μm as determined by a time-of-flight analytical method (Aerosizer, Amherst Process Instruments, Amherst, Mass.). As shown in FIG. 2, scanning electron microscopy (SEM) analysis showed the powders to be both hollow and porous. The tap density of the powder was determined to be less than 0.1 g/cm$^3$.

VI Preparation of Hollow Porous Particles of BDP by Spray-Drying

Perforated microstructures comprising beclomethasone dipropionate (BDP) particles were prepared by a spray-drying technique with a B-191 Mini Spray-Drier (Büchi, Flawil, Switzerland) under the following spray conditions: aspiration: 100%, inlet temperature: 85° C.; outlet temperature: 61° C.; feed pump: 10%; N$_2$ flow: 2,800 L/hr. The feed stock was prepared by mixing 0.11 g of lactose with a fluorocarbon-in-water emulsion immediately prior to spray drying. The emulsion was prepared by the technique described below.

74 mg of BDP (Sigma, Chemical Co., St. Louis, Mo.), 0.5 g of EPC-100-3 (Lipoid K G, Ludwigshafen, Germany), 15 mg sodium oleate (Sigma), and 7 mg of poloxamer 188 (BASF, Mount Olive, N.J.) were dissolved in 2 ml of hot methanol. The methanol was then evaporated to obtain a thin film of the phospholipid/steroid mixture. The phospholipid/steroid mixture was then dispersed in 64 g of hot deionized water (T=50 to 60° C.) using an Ultra-Turrax mixer (model T-25) at 8000 rpm for 2 to 5 minutes (T=60–70° C.). 8 g of perflubron (Atochem, Paris, France) was added dropwise during mixing. After the addition was complete, the emulsion was mixed for an additional period of not less than 4 minutes. The resulting coarse emulsion was then passed through a high pressure homogenizer (Avestin, Ottawa, Canada) at 18,000 psi for 5 passes. This emulsion was then used to form the feed stock which was spray dried as described above. A free flowing white powder was collected at the cyclone separator. The hollow porous BDP particles had a tap density of less than 0.1 g/cm$^3$.

VII Preparation of Hollow Porous Particles of TAA by Spray-Drying

Perforated microstructures comprising triamcinolone acetonide (TAA) particles were prepared by a spray drying technique with a B-191 Mini Spray-Drier (Büchi, Flawil, Switzerland) under the following spray conditions: aspiration: 100%, inlet temperature: 85° C.; outlet temperature: 61° C.; feed pump: 10%; N2 flow: 2,800 L/hr. The feed stock was prepared by mixing 0.57 g of lactose with a fluorocarbon-in-water emulsion immediately prior to spray drying. The emulsion was prepared by the technique described below.

100 mg of TAA (Sigma, Chemical Co., St. Louis, Mo.), 0.56 g of EPC-100-3 (Lipoid K G, Ludwigshafen, Germany), 25 mg sodium oleate (Sigma), and 13 mg of poloxamer 188 (BASF, Mount Olive, N.J.) were dissolved in 2 ml of hot methanol. The methanol was then evaporated to obtain a thin film of the phospholipid/steroid mixture. The phospholipid/steroid mixture was then dispersed in 64 g of hot deionized water (T=50 to 60° C.) using an Ultra-Turrax mixer (model T-25) at 8000 rpm for 2 to 5 minutes (T=60–70° C.). 8 g of perflubron (Atochem, Paris, France) was added dropwise during mixing. After the fluorocarbon was added, the emulsion was mixed for at least 4 minutes. The resulting coarse emulsion was then passed through a high pressure homogenizer (Avestin, Ottawa,.Canada) at 18,000 psi for 5 passes. This emulsion was then used to form the feed stock which was spray dried as described above. A free flowing white powder was collected at the cyclone separator. The hollow porous TAA particles had a tap density of less than 0.1 g/cm$^3$.

VIII Preparation of Hollow Porous Particles of DNase I by Spray-Drying

Hollow porous DNase I particles were prepared by a spray drying technique with a B-191 Mini Spray-Drier (Büchi, Flawil, Switzerland) under the following conditions: aspiration: 100%, inlet temperature: 80° C.; outlet temperature: 61° C.; feed pump: 10%; N$_2$ flow: 2,800 L/hr. The feed was prepared by mixing two solutions A and B immediately prior to spray drying.

Solution A: 20 g of water was used to dissolve 0.5 gr of human pancreas DNase I (Calbiochem, San Diego Calif.) and 0.012 g of poloxamer 188 NF grade (BASF, Mount Olive, N.J.).

Solution B: A fluorocarbon-in-water emulsion stabilized by phospholipid was prepared in the following way. The phospholipid, 0.52 g EPC-100-3 (Lipoid K G, Ludwigshafen, Germany), was homogenized in 87 g of hot deionized water (T=50 to 60° C.) using an Ultra-Turrax mixer (model T-25) at 8000 rpm for 2 to 5 minutes (T=60–70° C.). 13 g of perflubron (Atochem, Paris, France) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes.

Solutions A and B were combined and fed into the spray dryer under the conditions described above. A free flowing pale yellow powder was collected at the cyclone separator. The hollow porous DNase I particles had a volume-weighted mean aerodynamic diameter of 1.29±1.40 $\mu$m as determined by a time-of-flight analytical method (Aerosizer, Amherst Process Instruments, Amherst, Mass.). Scanning electron microscopy (SEM) analysis showed the powders to be both hollow and porous. The tap density of the powder was determined to be less than 0.1 g/cm$^3$.

The foregoing example further illustrates the extraordinary compatibility of the present invention with a variety of bioactive agents. That is, in addition to relatively small hardy compounds such as steroids, the preparations of the present invention may be formulated to effectively incorporate larger, fragile molecules such as peptides, proteins and genetic material.

IX Preparation of Hollow Porous Powder by Spray Drying a Gas-in-water Emulsion The following solutions were prepared with water for injection:

Solution 1:

| | |
|---|---|
| 3.9% w/v | m-HES hydroxyethylstarch (Ajinomoto, Tokyo, Japan) |
| 3.25% w/v | Sodium chloride (Mallinckrodt, St. Louis, MO) |
| 2.83% w/v | Sodium phosphate, dibasic (Mallinckrodt, St. Louis, MO) |
| 0.42% w/v | Sodium phosphate, monobasic (Mallinckrodt, St. Louis, MO) |

-continued

Solution 2:

0.45% w/v  Poloxamer 188 (BASF, Mount Olive, NJ)
1.35% w/v  Hydrogenated egg phosphatidylcholine, EPC-3 (Lipoid KG, Ludwigshafen, Germany)

The ingredients of solution 1 were dissolved in warm water using a stir plate. The surfactants in solution 2 were dispersed in water using a high shear mixer, The solutions were combined following emulsification and saturated with nitrogen prior to spray drying.

The resulting dry, free flowing, hollow, spherical product had a mean particle diameter of 2.6±1.5 µm. The particles, which may be used for the replacement or augmentation of lung surfactant, were spherical and porous as determined by SEM.

The previous example illustrates the point that, a wide variety of blowing agents (here nitrogen) may be used to provide microstructures exhibiting desired morphology. Indeed, one of the primary advantages of the present invention is the ability to after formation conditions so as to preserve biological activity (i.e. with proteins or lung surfactant) or produce microstructures having selected porosity.

X Preparation of Perforated Microstructure Powder Containing Ampicillin

The following materials were obtained and used to provide a feed stock:

20% w/w Ampicillin, Biotech grade (Fisher Scientific, Pittsburgh, Pa.)

14.38% w/w Hydroxyethyl starch (Ajinomoto, Japan)

65.62% w/w Dipalmitoylphosphatidylcholine (Genzyme, Cambridge, Mass.)

Perfluorohexane (3M, St. Paul, Minn.)

Deionized water

Hydroxyethyl starch, (HES; 0.9 g), and dipalmitoylphosphatidylcholine (DPPC; 4.11 g) were dispersed in 75 ml deionized water using an Ultra-Turrax mixer (model T-25) at 10,000 rpm for approximately 2 minutes (T=45–50° C.). The resulting DPPC/HES dispersion was chilled in an ice bath. Ampicillin (1.25 g) was added and allowed to mix for 1 minute (T=5–0° C.). Perfluorohexane (PFH, 4.11 g ) was then added dropwise during mixing (T=5–10° C.). After the addition was complete, the PFH-in-water emulsion was mixed on the Ultra-Turrx for a total of not less than 4 minutes.

A perforated microstructure powder comprising ampicillin was obtained by spray-drying (Büchi, 191 Mini Spray Dryer, Switzerland) the ampicillin containing emulsion at a rate of 5.5 ml/min. The inlet and outlet temperatures of the spray dryer were 90° C. and 55° C. respectively. The nebulization air and aspiration flows were 1,800 L/hr and 100% respectively. A free flowing white powder comprising porous microspheres was obtained.

XI Effect of Spray Drying on the In-Vitro Activity of Lung Surfactant

The activity of a spray dried lung surfactant preparation to lower the surface tension of a pulsating bubble was compared with the neat lung surfactant preparation. Bovine derived lung surfactant, Alveofact (Thomae, Biberach, Germany) and spray-dried lung surfactant containing microshells were dissolved in normal saline at a concentration of 10 mg/ml and allowed to incubate for 15 minutes at 37° C. Prior to analysis, the surfactant test solutions were vigorously shaken using a Vortex mixer for 30 seconds. The samples were analyzed for their surface properties using the Pulsating Bubble Surfactometer at 37° C. (model EC-PBS-B, Electronics, Amherst, N.Y.) according to the manufacturers instructions. Surfactant solutions were allowed to adsorb at minimum bubble diameter for 10 seconds, and bubble cycling was performed in the automatic mode (20 cycles/minute). For each experiment, measurements were taken for approximately the first 10 cycles, then again at t=2, 4, and 6 minutes.

The main difference observed between the neat and spray dried surfactant suspensions is the rate at which they adsorb to the bubble surface and thus lower the tension. The spray-dried materials required 6 cycles to achieve low surface tension as compared with one cycle for the Alveofact sample. However, the magnitude of the tension at maximum, and minimum bubble diameter were found to be approximately the same.

For the Alveofact dispersion, the tension decreased from 32 mN/m at maximum diameter to 4 mN/m at minimum in the first cycle. With further pulsation, a steady state oscillation was reached with a maximum tension $Y_{max}$≈33 mN/m and a minimum tension $Y_{min}$≈0 to 1 mN/m. For the spray-dried lung microshell dispersion, the tension decreased from 36 mN/m at maximum diameter to 16 mN/m at minimum in the first cycle. By the sixth pulsation, $Y_{max}$ and $Y_{min}$ were respectively 36 and 2 mN/m. Both the neat Alveofact and the spray-dried lung surfactant perforated microstructures satisfy the maximum and minimum surface tension requirements for physiologically effective lung surfactants as outlined by Notter; [R. H. Notter, in Surfactant Replacement Therapy, (Eds: D. H. Shapiro, and R. H. Notter) Alan R. Liss, New York, 1989] these values should range from≈35 to about 5 mN/m, respectively. This example illustrates that the compositions and methods of the present invention are particularly useful for the replacement or augmentation of lung surfactant in patients in need thereof.

XII Preparation of Perforated Microstructure Powder Containing Insulin

The following materials were obtained and used to provide a feed stock:

0.0045% w/w Human Insulin, (CalBiochem, San Diego, Calif.)

17.96% w/w Hydroxyethyl starch (Ajinomoto, Japan)

82.04% w/w Dipalmitoylphosphatidylcholine (Genzyme, Cambridge, Mass.)

Perfluorohexane (3M, St. Paul, Minn.)

Deionized water

Hydroxyethyl starch, (HES; 1.35 g) and dipalmitoylphosphatidylcholine (DPPC; 6.16 g) were dispersed in 100 ml deionized water using an Ultra-Turrax mixer (model T-25) at 10,000 rpm for approximately 2 minutes (T=45–50° C.). The resulting DPPC/HES dispersion was then chilled in a ice bath. Insulin (3.4 mg) was added and allowed to mix for I minute (T=5–10° C.). Perfluorohexane (PFH, 6.16 g) was then added dropwise during mixing (T=5–10° C.). After the addition was complete, the resulting PFH-in-water emulsion was mixed with the Ultra-Turrax) for a total of not less than 4 minutes. The insulin microstructure powder was obtained using a Buchi model 191 mini spray dryer (Büchi, Switzerland). The insulin containing emulsion was fed at a rate of 5.5 ml/min. The inlet and outlet temperatures of the spray dryer were 80° C. and 45° C. respectively. The nebulization air and aspiration flows were 1,800 L/hr and 100% respectively. A free flowing, white powder comprising porous microspheres was obtained.

XIII Effect of Perflubron on the In-Vitro Activity of DNAse I

Bovine pancreas deoxyribonuclease I, (DNAse I, Calbiochem, San Diego, Calif.) was dispersed in perflubron (1 mg/ml) and allowed to incubate for 1 hour. The perflubron was then evaporated using a Savant Speed Vac™ (Farmingdale, N.Y.). The activity of the perflubron treated DNAse I to cleave the phosphodiester linkages of DNA was compared with an untreated DNAse preparation. Serial dilutions of a DNAse solution (1 mg/ml) was combined with 50 μg DNA and dissolved in 500 μL of a 10 mM Tris-HCl buffer (6.3 pH) which contained 0.15 mg/ml CaCl, and 8.77 mg/ml NaCl. The samples were placed on an orbital shaker and incubated at 37° C. for 30 minutes. The condition of the DNA in each sample after incubation was then examined electrophoretically over a 1% agarose gel which contained ethidium bromide for visualization. No difference in DNA cleavage was observed between the untreated and perflubron-treated DNAse I samples.

XIV The Preparation of DNAse Microdispersion in Perflubron

One milliliter of the following solution was prepared: 0.00001%, w/v, Bovine pancreas deoxyribonuclease I, (DNAse I) (Calbiochem, San Diego, Calif.) and 0.001% polyvinyl pyrrolidone (PVP) (Sigma, St. Louis, Mo.), was dissolved into a solution composed of 0.121%, w/v, tris (hydroxymethyl)-aminomethane (Sigma), 0.0000015%, w/v, $CaCl_2$-2H2O (Sigma) and 0.0000877% w/v, NaCl (Sigma). The pH of the solution was adjusted to 6.3 prior to adding the DNAse or PVP.

One hundred microliters of the DNAse/PVP solution was added to a 12×100 mm test tube containing 5 ml perfluorooctylethane (F-Tech, Japan). The tube was capped and submerged in a sonicator bath (Branson Model 3200, Danbury, Conn.) for 5 seconds to obtain a milky dispersion in the perflubron. The suspension was then evaporated to dryness using a Savant Speed Vac™ (Model SC 200). The resulting dried microspheres were resuspended with 7 ml Perflubron. A milky DNAse/PVP-in-perflubron suspension was obtained. Particle size analysis was done by laser diffraction (Horiba LA-700, Irvine, Calif.) in the volume-weighted mode. Approximately a 20 to 50 μL aliquot of each sample was diluted in 9 to 10 ml of n-dodecane. The distribution shape "3", refractive index ratio of 1.1 and the fraction cell was used. The resulting microdispersion had a mean droplet diameter of 2.83 μm. Examples XIII and XIV clearly demonstrate the feasibility of preparing enzymatically active stabilized dispersions in accordance with the present invention. This Example further illustrates that a number of techniques may be used to form compatible particulates useful in the disclosed dispersions.

XV Preparation of Fluorescent-Labeled Perforated Microstructure Powder via Spray Drying The following materials were obtained and used to manufacture feed stock:

0.2% w/w Nitrobenzoyldiol Phosphatidylcholine (Avanti Polar Lipids, Alabaster, Ala.)

17.6% w/w Hydroxyethyl starch (Ajinomoto, Japan)

82.2% w/w Dipalmitoylphosphatidylcholine (Genzyme, Cambridge, Mass.)

Perfluorohexane (3M, St. Paul, Minn.)

Deionized water

Dipalmitoylphosphatidylcholine (DPPC; 1 g) and nitrobenzoyldiol phosphatidylcholine (NBD-PC; 10 mg) were dissolved in 4 ml chloroform. The chloroform was then removed using a Savant Speed Vac™ (Model SC 200). Hydroxyethyl starch, (HES; 0.9 g), dipalmitoylphosphatidyl-choline (DPPC; 3.19 g) and 75 ml deionized water were then added to the DPPC/NBD-PC thin film. The surfactants and starch were then dispersed in the aqueous phase using an Ultra-Turrax mixer (model T-25) at 10,000 rpm for approximately 2 minutes (T=45–50° C.). The resulting NBD-PC/DPPC/HES dispersion was chilled in an ice bath. Perfluorohexane (PFH, 4.11 g ) was then added dropwise during mixing (T=5–10° C.). After the addition was complete, the resulting PFH-in-water emulsion was mixed on the Ultra-Turrax for an additional time of not less than 4 minutes. The fluorescently labeled microshell powder was obtained by spray drying (Büuchi, 191 Mini Spray Dryer, Switzerland). The NBD-PC/DPPC/HES containing emulsion was fed at a rate of 5.5 ml/min. The inlet and outlet temperatures of the spray dryer were 100° C. and 65° C. respectively. The nebulization air and aspiration flows were 1,800 Llhr and 100% respectively. A free flowing, yellow powder comprising perforated microstructures was obtained.

XVI Inhalation Behavior of a Perforated Microstructure in Fluorocarbon Dispersion vs. Aqueous Liposomes The nebulization profile as a function of the aerodynamic diameter of a spray-dried microshell-in-perflubron dispersion vs. an aqueous-based liposomal dispersion was evaluated using an Andersen Cascade Impactor. For the experiments, compressed air served as the carrier and aerosol generating gas. An air flow rate of 7.5 liters/min. was established at a pressure of 20 p.s.i. Aerosols were generated with a DeVilbiss air-jet nebulizer (DeVilbiss Co., Somerset, Pa.). The nebulizer was connected to an Andersen cascade impactor (Sierra-Andersen 1 ACFM Nonviable Ambient Particle Sizing Sampler). The aqueous liposomal dispersion was prepared by dispersing fluorescent-labeled microshells prepared as set forth in Example XIV in water, followed by sonification with a Vibracell™ sonicator (Sonics Materials, 30 mm o.d. titanium probe) at a power of 100 watts for approximately 2 minutes (T=22–25° C.). The same perforated microstructures were suspended in PFOB to provide a stabilized dispersion. 5 ml of either a 20 mg/ml fluorescentlylabeled microshell-in-PFOB dispersion or the aqueous fluorescently-labeled liposomes were nebulized for 4 minutes. The 8 stages of the impactor were then washed with chloroform:methanol (2:1 v/v). Each stage extract was then transferred to a 2 milliliter volumetric flask and q.s. to the mark with chloroform:methanol (2:1 v/v).

The extracts were measured for fluorescence content using the following conditions: $\lambda_{ex}$=481 nm; $\lambda_{em}$=528 nrm and quantified by comparison to an external standard curve. Table III lists the characteristics of each cascade impactor stage, the inhalation behavior of the nebulized microshells and liposomes. The NBD-PC mass distribution as a function of aerodynamic diameter was calculated using calibration curves described by Gonda, et. al., [Gonda, I., Kayes, J. B., Groom, C. V., and Fildes, F. J. T.; Characterization of hydroscopic inhalation aerosols. In: Particle Size Analysis 1981 (Eds. N. G. Stanlet-Wood, and T. Allen), pp. 31–43, Wiley Heyden Ltd, New York] and incorporated herein by reference.

Comparison of the two delivery vehicles revealed that the efficiency of nebulization was greater for the liposomes. On the other hand, a higher percentage of the nebulized dose to smaller airway diameters could be achieved with the fluorocarbon-delivered microstructures, which is reflection of it's smaller median mass aerodynamic diameter (MMAD), achieved due its hollow, porous nature. This Example and. the results shown in Table III immediately below clearly illustrate that a number of different colloidal systems, including both particulate dispersions and liposomal preparations, are compatible with the present invention.

TABLE III

Median Mass Aerodynamic Diameters of Hollow Microspheres vs. Liposomes

| Impactor Stage | Simulated Particle Diameter | Simulated Lung Region | Microstructure [NBD-PC] (μm) | Liposomes [NBD-PC] (μm) |
|---|---|---|---|---|
| 0 | 9–10 μm | | 0.0476 | 0.353 |
| 1 | 5.8–9.0 μm | Pharynx | 0.216 | 0.974 |
| 2 | 4.7–5.8 μm | Trachea & Primary Bronchi | 0.55 | 2.19 |
| 3 | 3.3–4.7 μm | Secondary bronchi | 1.83 | 3.03 |
| 4 | 2.1–3.3 μm | Terminal bronchi | 1.81 | 0.594 |
| 5 | 1.1–2.10 μm | Alveoli | 0.821 | 0.0214 |
| 6 | 0.65–1.1 μm | Alveoli | 0.0317 | 0 |
| 7 | 0.43–0.65 μm | Alveoli | 0 | 0 |
| | | MMAD | 2.6 μm | 3.9 μm |

XVII Andersen Impactor Test for Assessing Aerosol Performance

Formulations described in Examples XVIII, XIX, XX and XXI comprising Cromolyn sodium were tested using commonly accepted pharmaceutical procedures. The method utilized was compliant with the United State Pharmacopeia (USP) procedure (Pharrnacopeial Previews (1996) 22:3065–3098) incorporated herein by reference. The Andersen Impactor was associated with the respective nebulizer or metered dose inhaler as set forth in the following examples and collected aerosolized sample for a specified period.

Extraction procedure. The extraction from all the plates, induction port, and actuator were performed in closed vials with 10 mL of a suitable solvent. The filter was installed but not assayed, because the polyacrylic binder interfered with the analysis. The mass balance and particle size distribution trends indicated that the deposition on the filter was negligibly small. The plates were extracted with deionized water.

Quantitation procedure. Cromolyn sodium was quantitated by absorption spectroscopy (Beckman DU640 spectrophotometer) relative to an external standard curve with the extraction solvent as the blank. Cromolyn sodium was quantitated using the absorption peak at 326 nm.

Calculation procedure. For each formulation, the mass of the drug in the device as well as on the induction port (-1) and plates (0–7) were quantified as described above. The Fine Particle Dose and Fine Particle Fraction was calculated according to the USP method referenced above. Throat deposition was defined as the mass of drug found in the induction port and on plates 0 and 1. The mean mass aerodynamic diameters (MMAD) and geometric standard diameters (GSD) were evaluated by fitting the experimental cumulative function with log-normal distribution by using two-parameter fitting routine. The results of such measurements are presented in subsequent examples.

XVIII Nebulization of Porous Particulate Structures Comprising Phospholipids and Cromolyn sodium in Perfluorooctylethane using a MicroMist™ Nebulizer Forty milligrams of the lipid based microspheres containing 50% cromolyn sodium by weight (as from Example V) were dispersed in 10 ml perfluorooctylethane (PFOE) by shaking, forming a suspension. The suspension was nebulized until the fluorocarbon liquid was delivered or had evaporated using a Micro Mist™ (DeVilbiss) disposable nebulizer using a PulmoAide® air compressor (DeVilbiss). As described above an Andersen Cascade Impactor was used to measure the resulting particle size distribution. The impactor was disassembled and the plates of the impactor were extracted with water. Cromolyn sodium content was measured by UV adsorption at 326 nm. The fine particle fraction is the ratio of particles deposited in stages 2 through 7 to those deposited in all stages of the impactor. The fine particle mass is the weight of material deposited in stages 2 through 7. The deep lung fraction is the ratio of particles deposited in stages 5 through 7 of the impactor (which correlate to the alveoli) to those deposited in all stages. The deep lung mass is the weight of material deposited in stages 5 through 7. Table IV immediately below provides a summary of the results.

TABLE IV

| Fine particle fraction | fine particle mass | deep lung fraction | deep lung mass |
|---|---|---|---|
| 90% | 6 mg | 75% | 5 mg |

XIX Nebulization of Porous Particulate Structures Comprising Phospholipids and Cromolyn Sodium in Perfluorooctylethane using a Raindrop® Nebulizer A quantity of lipid based microspheres containing 50% cromolyn sodium, as from Example V, weighing 40 mg was dispersed in 10 ml perfluorooctylethane (PFOE) by shaking, thereby forming a suspension. The suspension was nebulized until the fluorocarbon liquid was delivered or had evaporated using a Raindro® disposable nebulizer (Nellcor Puritan Bennet) connected to a PulmoAide® air compressor (DeVilbiss). An Andersen Cascade Impactor was used to measure the resulting particle size distribution in the manner described in Examples XVII and XVIII. Table V immediately below provides a summary of the results.

TABLE V

| Fine particle fraction | fine particle mass | Deep lung fraction | deep lung mass |
|---|---|---|---|
| 90% | 4 mg | 80% | 3 mg |

XX Nebulization of Aqueous Cromolyn Sodium Solution

The contents of plastic vial containing a unit dose inhalation solution of 20 mg of cromolyn sodium in 2 ml purified water (Dey Laboratories) was nebulized using a Micro Mist™ disposable nebulizer (DeVilbiss) using a PulmoAide® air compressor (DeVilbiss). The cromolyn sodium solution was nebulized for 30 minutes. An Andersen Cascade Impactor was used to measure the resulting particle size distribution, by the method described above in Example XVII. Table VI immediately below provides a summary of the results. In this regard, it will be appreciated that, the formulations nebulized from fluorocarbon suspension mediums in Examples XVIII and XIX provided a greater percentage of deep lung deposition than the aqueous solution.

TABLE VI

| fine particle fraction | fine particle mass | Deep lung fraction | deep lung mass |
|---|---|---|---|
| 90% | 7 mg | 60% | 5 mg |

XXI Preparation of a Metered Dose Inhaler of Cromolyn Sodium

A pre-weighed amount of hollow porous cromolyn sodium particles prepared in Example V was placed into a 10 ml aluminum can and dried in a vacuum oven under the flow of nitrogen for 3–4 hours at 40° C. The amount of powder filled into the can was determined by the amount of drug required to provide a desired therapeutic effect. After this the can was crimp-sealed using a DF31/50act 50 μl valve (Valois of America, Greenwich, Conn.) and filled with HFA-134a propellant (DuPont, Wilmington Del.) by overpressure through the stem. The amount of propellant in the can was determined by weighing the can before and after the fill.

The filled MDI was then used to compare the administration of cromolyn sodium using a metered dose inhaler and a neubulizer. More specifically, a cromolyn sodium preparation was nebulized and quantitated as described in Example XVIII. The MDI was then associated with the Andersen impactor and discharged. For the test, 5 shots were sent to waste and, 20 shots were made into the Andersen impactor.

Figure 3:
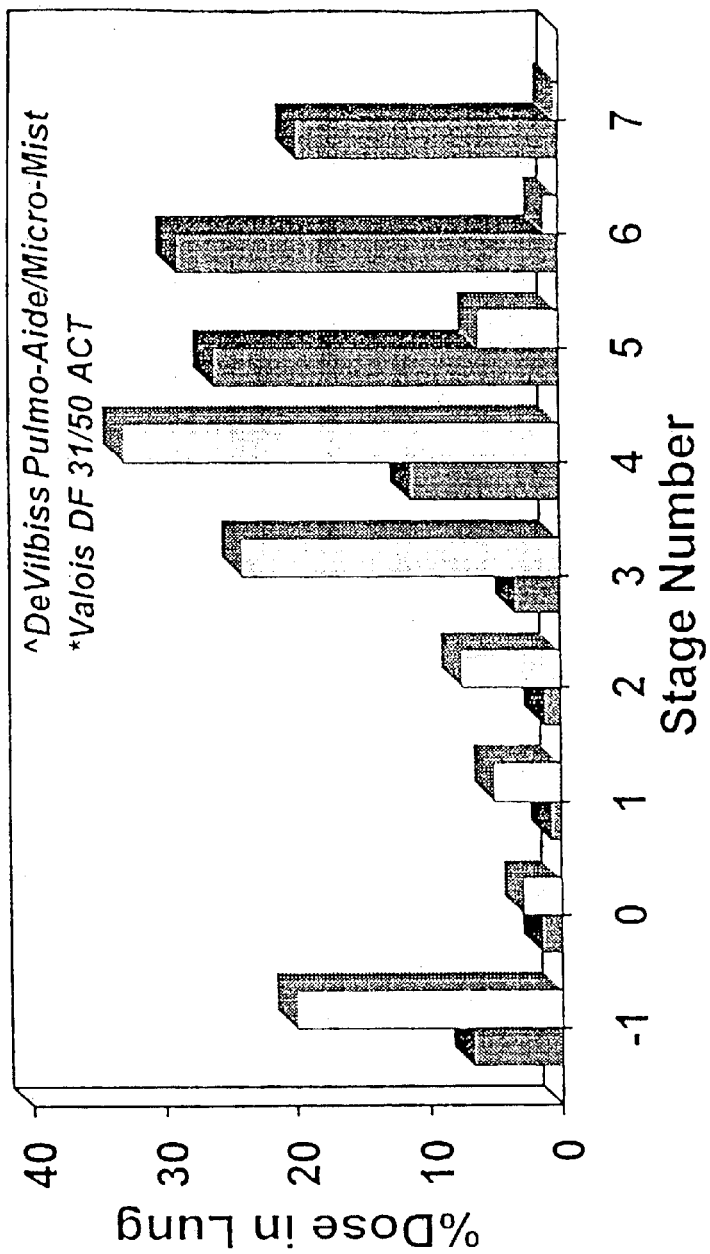
FIG. 3 presents results of in-vitro Andersen cascade impactor studies comparing the same hollow porous cromolyn sodium formulation delivered via MDI in HFA-134a, or from a long-chain fluorocarbon (perfluorooctyl ethane) via nebulization. Nebulized particles are observed to deposit onto later stages in the impactor, corresponding to improved systemic delivery in-vivo.

A comparison of the Andersen cascade impactor results for the nebulized cromolyn sodium and the cromolyn sodium administered by the MDI is shown in FIG. 3. As seen in the Figure, a significantly greater percentage of the nebulized drug is found on plates 5–7 showing the enhanced potential for systemic delivery via nebulization.

XXII Nebulization of Porous Particulate Structures Comprising Mixtures of Long-Chain/Short-Chain Phospbolipids and Albuterol Sulfate in Perflubron To further demonstrate the diversity of the present invention the spray dried powder from Example IV was dispersed in perflubron (Atochem, France) at 0.2 wt% concentration. The resulting stabilized dispersion did not show any visible sedimentation over 30 minutes and could be easily nebulized with a Pulmo-Neb Disposable Nebulizer (DeVilbiss, Somerset, Pa.). A significant deposition of the powder was found on plates 4 and 5 of an Andersen cascade impactor, as judged by visual inspection, indicating that significant deposition is likely in human secondary and terminal bronchi.

Those skilled in the art will further appreciate that the present invention may be embodied in other specific forms without departing from the spirit or central attributes thereof. In that the foregoing description of the present invention discloses only exemplary embodiments thereof, it is to be understood that, other variations are contemplated as being within the scope of the present invention. Accordingly, the present invention is not limited to the particular embodiments which have been described in detail herein. Rather, reference should be made to the appended claims as indicative of the scope and content of the invention.

What is claimed is:

1. A method for the pulmonary delivery of one or more bioactive agents comprising the steps of:
   providing a stabilized respiratory dispersion comprising one or more bioactive agents wherein the respiratory dispersion comprises a plurality of perforated microstructures suspended in and substantially permeated by a fluorochemical continuous phase wherein the volume of suspension medium displaced by the perforated microstructure is less than 70% of the average particle volume of the perforated microstructure;
   nebulizing said respiratory dispersion with a nebulizer to provide an aerosolized medicament; and
   administering a therapeutically effective amount of said aerosolized medicament to at least a portion of the pulmonary passages of a patient in need thereof.

2. The method of claim 1 wherein the mean aerodynamic diameter of the perforated microstructures is between 0.5 and 5 μm.

3. The method of claim 1 wherein said perforated microstructures comprise a surfactant.

4. The method of claim 3 wherein said surfactant is selected from the group consisting of phospholipids, nonionic detergents, nonionic-block copolymers, ionic surfactants, biocompatible fluorinated surfactants and combinations thereof.

5. The method of claim 3 wherein said surfactant is a phospholipid.

6. The method of claim 5 wherein said phospholipid is selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine and combinations thereof.

7. The method of claim 1 wherein said bioactive agent is selected from the group consisting of antiallergics, bronchodilators, pulmonary lung surfactants, analgesics, antibiotics, leukotriene inhibitors or antagonists, antihistamines, antiinflammatories, antineoplastics, anticholinergics, anesthetics, anti-tuberculars, imaging agents, cardiovascular agents, enzymes, steroids, genetic material, viral vectors, antisense agents, proteins, peptides and combinations thereof.

8. The method of claim 1 wherein said bioactive agent is delivered to the systemic circulation of said patient.

9. An inhalation system for the pulmonary administration of a bioactive agent to a patient comprising:
   a fluid reservoir;
   a stable respiratory dispersion in said fluid reservoir wherein said stabilized dispersion comprises a fluorochemical continuous phase and a plurality of perforated microstructures comprising at least one bioactive agent suspended in and substantially permeated by the continuous phase wherein the volume of suspension medium displaced by the perforated microstructure is less than 70% of the average particle volume of the perforated microstructure; and a nebulizer operably associated with said fluid reservoir wherein the nebulizer is capable of aerosolizing and discharging the stable respiratory dispersion.

10. The system of claim 9 wherein said perforated microstructures comprise a surfactant.

11. The system of claim 10 wherein said surfactant is selected from the group consisting of phospholipids, non-ionic detergents, nonionic block copolymers, ionic surfactants, biocompatible fluorinated surfactants and combinations thereof.

12. The system of claim 10 wherein said surfactant is a phospholipid.

13. The system of claim 12 wherein said phospholipid is selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine and combinations thereof.

14. The system of claim 9 wherein the mean aerodynamic diameter of the perforated microstructures is between 0.5 and 5 μm.

15. The system of claim 9 wherein said bioactive agent is selected from the group consisting of antiallergics, bronchodilators, pulmonary lung surfactants, analgesics, antibiotics, antiinfectives, leukotriene inhibitors or antagonists, antihistamine, antiinflammatories, antineoplastics, antocholinergics, anesthetics, antituberculars, imaging agents, cardiovascular agents, enzyme, steroids, genetic material, viral vectors, antisense agents, proteins, peptides and combinations thereof.

16. The system of claim 9 wherein said bioactive agent comprises a compound selected from the group consisting of proteins, peptides and genetic material.

17. The system of claim 9 wherein said fluid reservoir is a multi-dose reservoir or a single dose reservoir.

18. The system of claim 9 wherein said nebulizer is a jet nebulizer, an ultrasonic nebulizer or a single-bolus nebulizer.

19. The system of claim 9 wherein the respiratory dispersion comprises a creaming time of greater than 1 minute.

20. The system of claim 9 wherein the respiratory dispersion comprises a creaming time of greater than 30 minutes.

21. The system of claim 9 wherein the perforated microstructures comprise a geometric diameter of 1–30 μm.

22. The system of claim 15 wherein the bioactive agent is an antiinfective selected from the group consisting of cephalosporines, macrolides, quinoline, penicillins, streptomycin, sulphonamides, tetracyclines, and pentamidine.

* * * * *